US012767993B2

(12) United States Patent
Kim et al.

(10) Patent No.: US 12,767,993 B2
(45) Date of Patent: Oct. 20, 2026

(54) **SINGLE-STRANDED NUCLEIC ACID APTAMERS SPECIFICALLY BINDING TO *CRONOBACTER* AND KIT FOR DETECTING *CRONOBACTER* USING THE SAME**

(71) Applicant: KOREA INSTITUTE OF SCIENCE AND TECHNOLOGY, Seoul (KR)

(72) Inventors: Byoung Chan Kim, Seoul (KR); Hye Ri Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 579 days.

(21) Appl. No.: 18/324,552

(22) Filed: May 26, 2023

(65) Prior Publication Data

US 2024/0124943 A1 Apr. 18, 2024

(30) Foreign Application Priority Data

Oct. 14, 2022 (KR) ........................ 10-2022-0132622

(51) Int. Cl.

*C12Q 1/6816* (2018.01)
*C12Q 1/689* (2018.01)

(52) U.S. Cl.

CPC ........... *C12Q 1/689* (2013.01); *C12Q 1/6816* (2013.01)

(58) Field of Classification Search

None

See application file for complete search history.

(56) References Cited

FOREIGN PATENT DOCUMENTS

| | | | |
|---|---|---|---|
| EP | 2 287 333 | A1 | 2/2011 |
| KR | 10-1744376 | B1 | 6/2017 |
| KR | 10-2017-0099680 | A | 9/2017 |
| KR | 10-2018-0033748 | A | 4/2018 |
| KR | 10-2050509 | B1 | 11/2019 |
| KR | 10-2020-0059765 | A | 5/2020 |
| KR | 10-2243449 | B1 | 4/2021 |

OTHER PUBLICATIONS

Yu, Aptamers can Discriminate Alkaline Proteins with High Specificity, Chembiochem, 12(17): 2659-2666, 2011. (Year: 2011).*

Kim, Hye Ri, Myunghee Kim, and Byoung Chan Kim. "Specific detection of Cronobacter sakazakii in powdered infant formula using ssDNA aptamer." Analyst 146.11, 2021. (pp. 3534-3542).

Korean Office Action issued on Oct. 22, 2024, in corresponding Korean Patent Application No. 10-2022-0132622. (8pages in English, 6pages in Korean).

Kim, Hye Ri, et al., "Development of Multi-reactive aptamers for *Cronobacter* spp. using the sequential partitioning Method." The 2022 KSBB Spring Meeting and International Symposium (Apr. 14, 2022): 134-134.

* cited by examiner

*Primary Examiner* — Carolyn L Greene

(74) *Attorney, Agent, or Firm* — NSIP Law

(57) ABSTRACT

The present specification may provide a novel single-stranded nucleic acid aptamer capable of simultaneous detection of seven *Cronobacter* species, a composition or kit for multiple detection comprising the aptamer. The novel single-stranded nucleic acid aptamer of the disclosure can bind to all seven reclassified *Cronobacter* species, which are pathogenic bacteria, with high binding affinity due to its affinity and specificity. Therefore, the seven *Cronobacter* species can be easily and efficiently multi-detected from the environment where various bacteria are colonized and inhabited, and from contaminated food and water.

10 Claims, 17 Drawing Sheets

Specification includes a Sequence Listing.

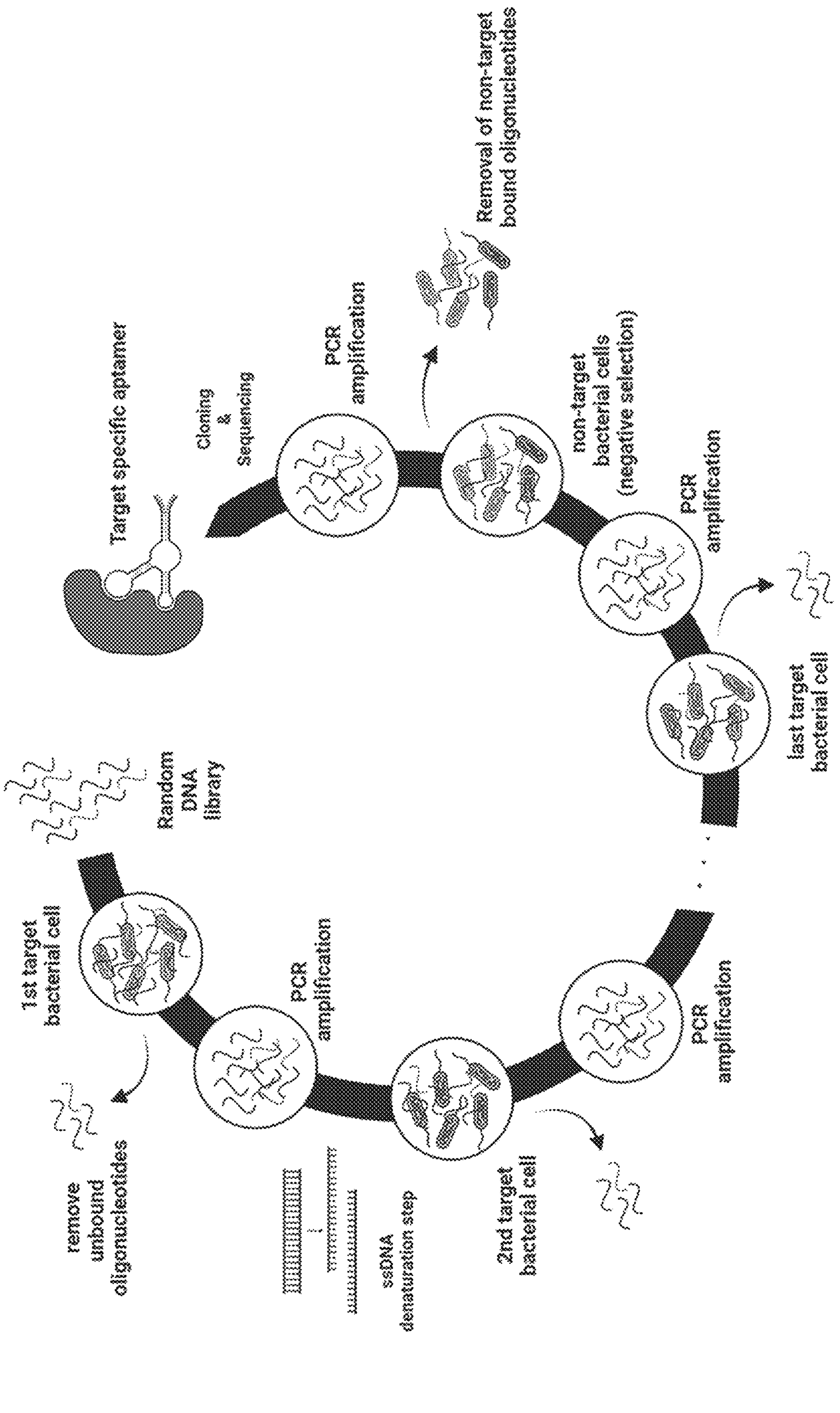

Target specific aptamer
Cloning & Sequencing
PCR amplification
Removal of non-target bound oligonucleotides
non-target bacterial cells (negative selection)
PCR amplification
last target bacterial cell
Random DNA library
1st target bacterial cell
PCR amplification
remove unbound oligonucleotides
ssDNA denaturation step
2nd target bacterial cell
PCR amplification

SINGLE-STRANDED NUCLEIC ACID APTAMERS SPECIFICALLY BINDING TO *CRONOBACTER* AND KIT FOR DETECTING *CRONOBACTER* USING THE SAME

CROSS REFERENCE TO RELATED APPLICATION

The present application claims priority to Korean Patent Application No. 10-2022-0132622, filed Oct. 14, 2022, the entire contents of which is incorporated herein for all purposes by this reference.

INCORPORATION-BY-REFERENCE OF MATERIAL SUBMITTED BY U.S.P.T.O. EFS-WEB

This application contains a Sequence Listing, which is being submitted in computer readable form via the United States Patent and Trademark Office Patent Center and which is hereby incorporated by reference in its entirety for all purposes. The XML file submitted herewith, which is named as "NewApp_0210690267_SequenceListing" and is created on May 26, 2023, contains a 7,583 bytes file.

BACKGROUND OF THE INVENTION

Field of the Invention

The present specification discloses a novel single-stranded nucleic acid aptamer, a *Cronobacter* detection kit comprising the same, and a detection method.

Description of Government-Sponsored Research

This research was conducted by the following national project.

Department name: Ministry of Science and ICT, Project management (specialized) organization name: Korea Institute of Science and Technology, Research project name: Support for research operation expenses (main project expense) for Korea Institute of Science and Technology, Research project name: atmospheric environment complex response research project, Project number: 2E31680, Project identification number: 1711173297

Description of the Related Art

Pathogen bacteria that cause disease live in a variety of environments. Pathogenic bacteria easily contaminate water or food and cause illness in people who consume them. In 2005, 1.8 million people died from diarrhea caused by ingestion of food and water contaminated with pathogenic bacteria. It is estimated that 76 million cases of disease are reported each year in the United States, 325,000 people are hospitalized, and 5,000 people die. Damage caused by pathogenic bacteria is expected to continue to increase due to the consumption of various foods. Accordingly, as disease management by food management has emerged as a major issue, a technology that can detect pathogenic bacteria in advance is required in industries related to food engineering and water quality.

*Cronobacter* spp. is known as a pathogenic bacterium is known as *Enterobacter sakazakii*, and reclassified by 16sRNA analysis into seven species 71*C. sakazakii, C. malonaticus, C. turicensis, C. muytjensii, C. dublinensis, C. condimenti, C. universalis*). The strain is resistant to osmotic pressure and a dry environment, so it is easy to live in various environments. In particular, there have been cases where the strain inhabited infant formula and infected infants, and other cases of *Cronobacter* infection have been reported in adults as well. Infection with *Cronobacter* causes sepsis, meningitis, encephalitis, necrotizing enterocolitis, etc., and has a high mortality rate of up to 80%, drawing attention from the food industry. In order to detect *Cronobacter*, a culture-based method for counting colonies through culture, an immuno-based assay, a polymerase chain reaction, and the like have been suggested, but there is a problem in that it is difficult to respond quickly to contamination due to the long time required to calculate the results, which makes it difficult to diagnose technically quickly.

SUMMARY OF THE INVENTION

An object to be achieved by the disclosure is to provide a single-stranded nucleic acid aptamer capable of simultaneously detecting seven *Cronobacter* species, and a composition or kit for multiplex detection comprising the aptamer.

An object to be achieved by the disclosure is to provide a method for detecting *Cronobacter* using a single-stranded nucleic acid aptamer.

An object to be achieved by the present disclosure is to provide a method for removing *Cronobacter* from a sample using a single-stranded nucleic acid aptamer.

In order to achieve the above object, one embodiment of the disclosure provides single-stranded nucleic acid aptamer comprising at least one nucleotide sequence of nucleotide sequences of SEQ ID NOs: 1 to 4, and specifically binding to seven *Cronobacter* species consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Another embodiment of the disclosure provides a composition for multi-detection of *Cronobacter*, which comprises the above single-stranded nucleic acid aptamer and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Still another embodiment of the disclosure provides a kit for detecting *Cronobacter*, which comprises the above single-stranded nucleic acid aptamer and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Still another embodiment of the disclosure provides a method for detecting *Cronobacter*, comprising contacting the single-stranded nucleic acid aptamer with a sample; and identifying whether a *Cronobacter*-aptamer complex is formed by contact of the single-stranded nucleic acid aptamer with *Cronobacter* in the sample.

Still another embodiment of the disclosure provides a method for removing *Cronobacter* from a sample comprising contacting the single-stranded nucleic acid aptamer with a sample to form a complex of *Cronobacter* and the single-stranded nucleic acid aptamer; and removing the complex.

The novel single-stranded nucleic acid aptamer according to one embodiment of the disclosure can bind to all seven reclassified species of the pathogenic bacterium *Cronobacter* with high binding affinity due to its affinity and specificity. According to the disclosure, seven *Cronobacter* species can be simultaneously multi-detected from an environment where various bacteria are colonized and inhabited, contaminated food, water, etc., so that it is convenient and efficient. Therefore, according to the disclosure, it is possible to detect seven *Cronobacter* species simply and quickly by applying to an aptamer-based sensor platform, and the aptamer can be used in various industrial fields such as food, biology, and environmental fields.

BRIEF DESCRIPTION OF THE DRAWINGS

FIG. 2 shows a schematic diagram of a SELEX method as another method for producing and selecting single-stranded nucleic acid aptamers according to an embodiment of the disclosure.

DETAILED DESCRIPTION OF THE INVENTION

Figure 1:
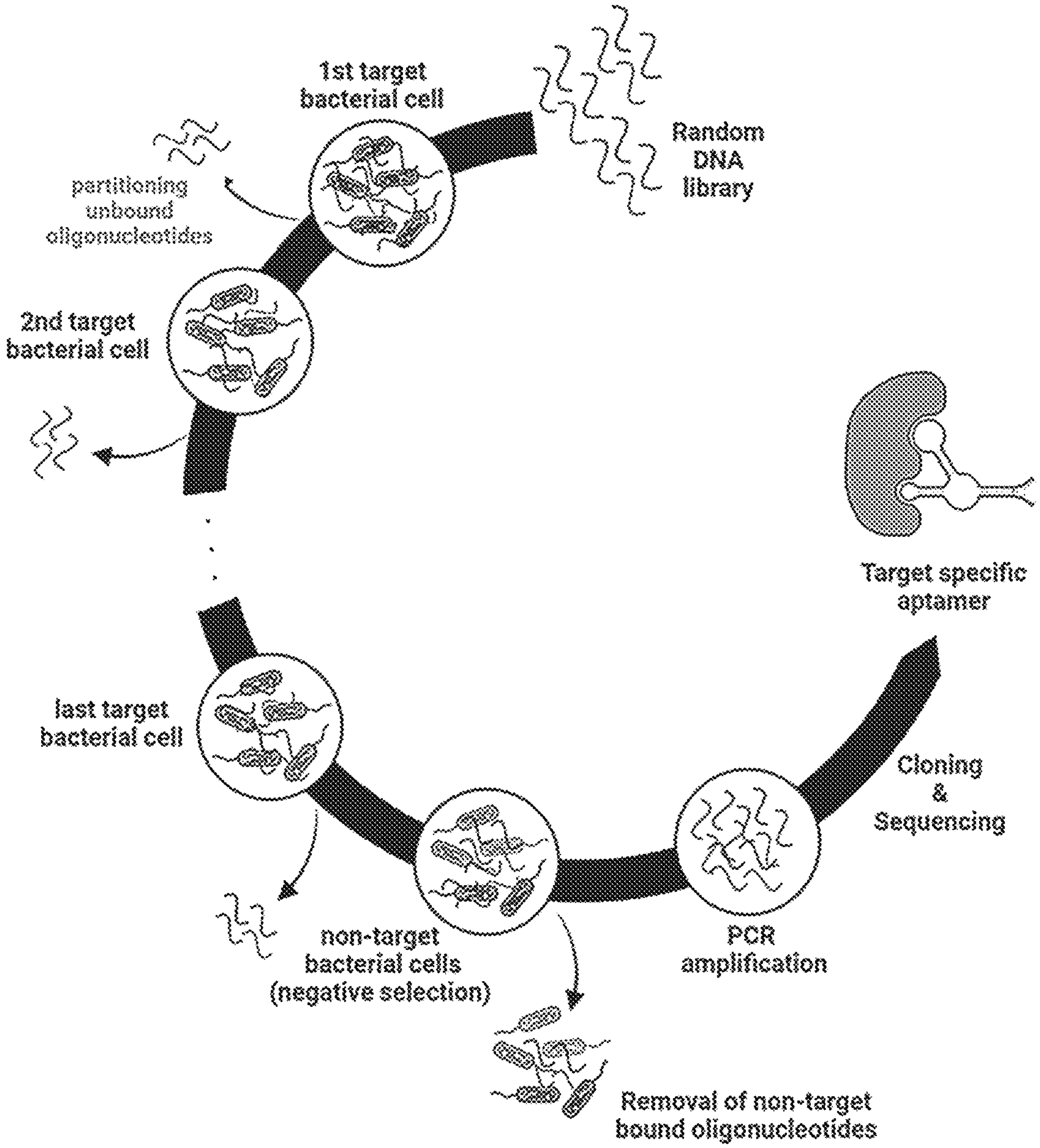
FIG. 1 is a schematic diagram of a sequential partitioning method for producing and selecting single-stranded nucleic acid aptamers that specifically bind to seven *Cronobacter* species according to an embodiment of the disclosure.
Figure 3A:
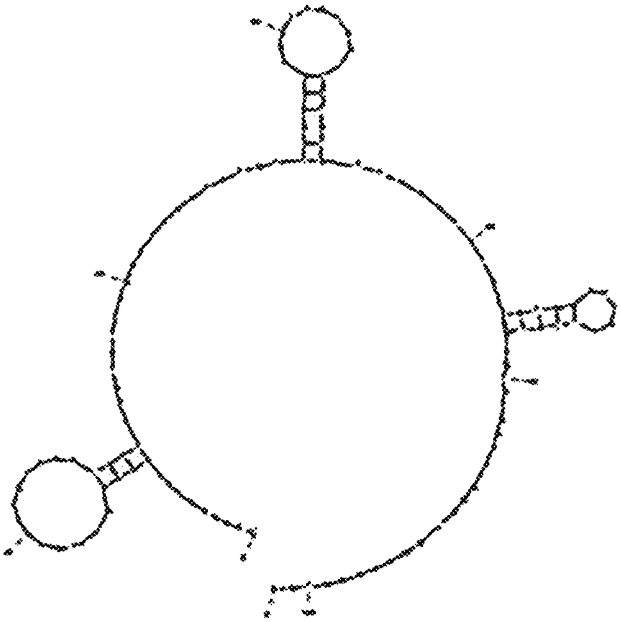
FIG. 3A is a diagram showing the analysis of the 2D structure of ssDNA aptamer (C1) according to an embodiment of the present disclosure.
Figure 3B:
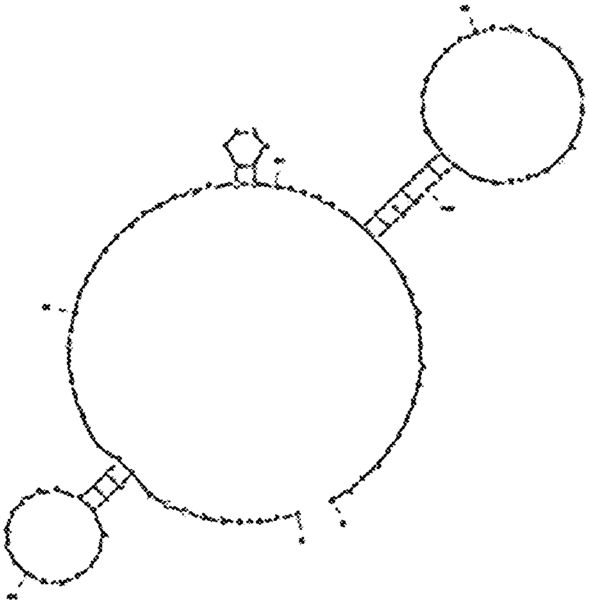
FIG. 3B is a diagram showing the analysis of the 2D structure of ssDNA aptamer (C2) according to an embodiment of the present disclosure.
Figure 3C:
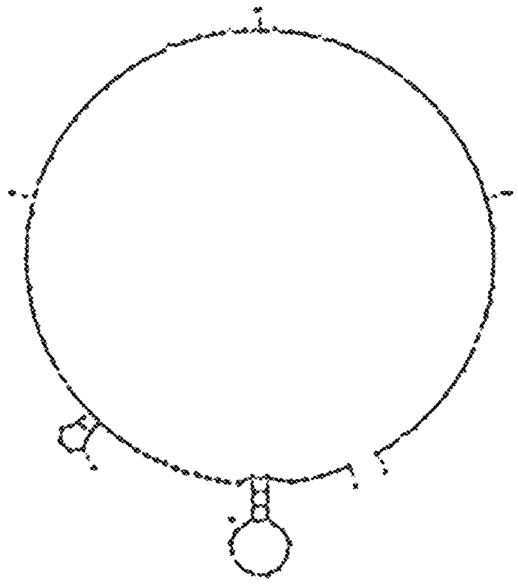
FIG. 3C is a diagram showing the analysis of the 2D structure of ssDNA aptamer (C7) according to an embodiment of the present disclosure.
Figure 3D:
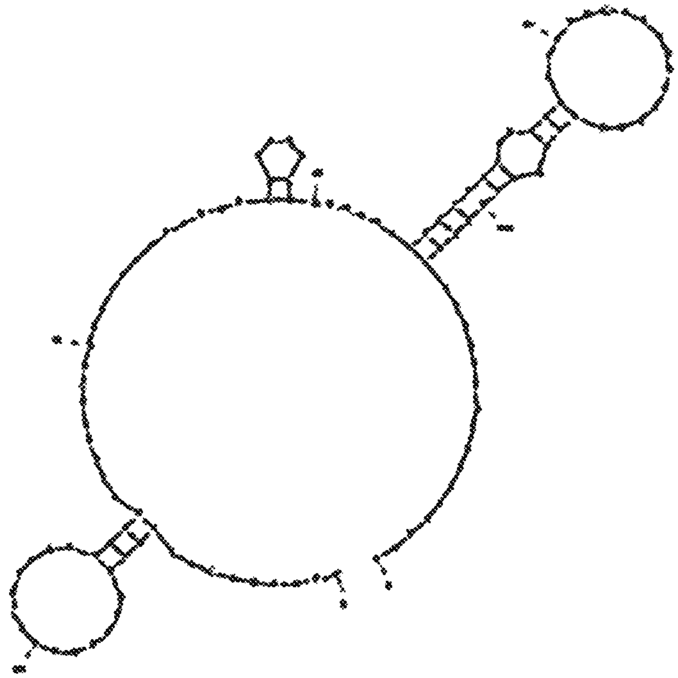
FIG. 3D is a diagram showing the analysis of the 2D structure of ssDNA aptamer (C9) according to an embodiment of the present disclosure.
Figure 4A:
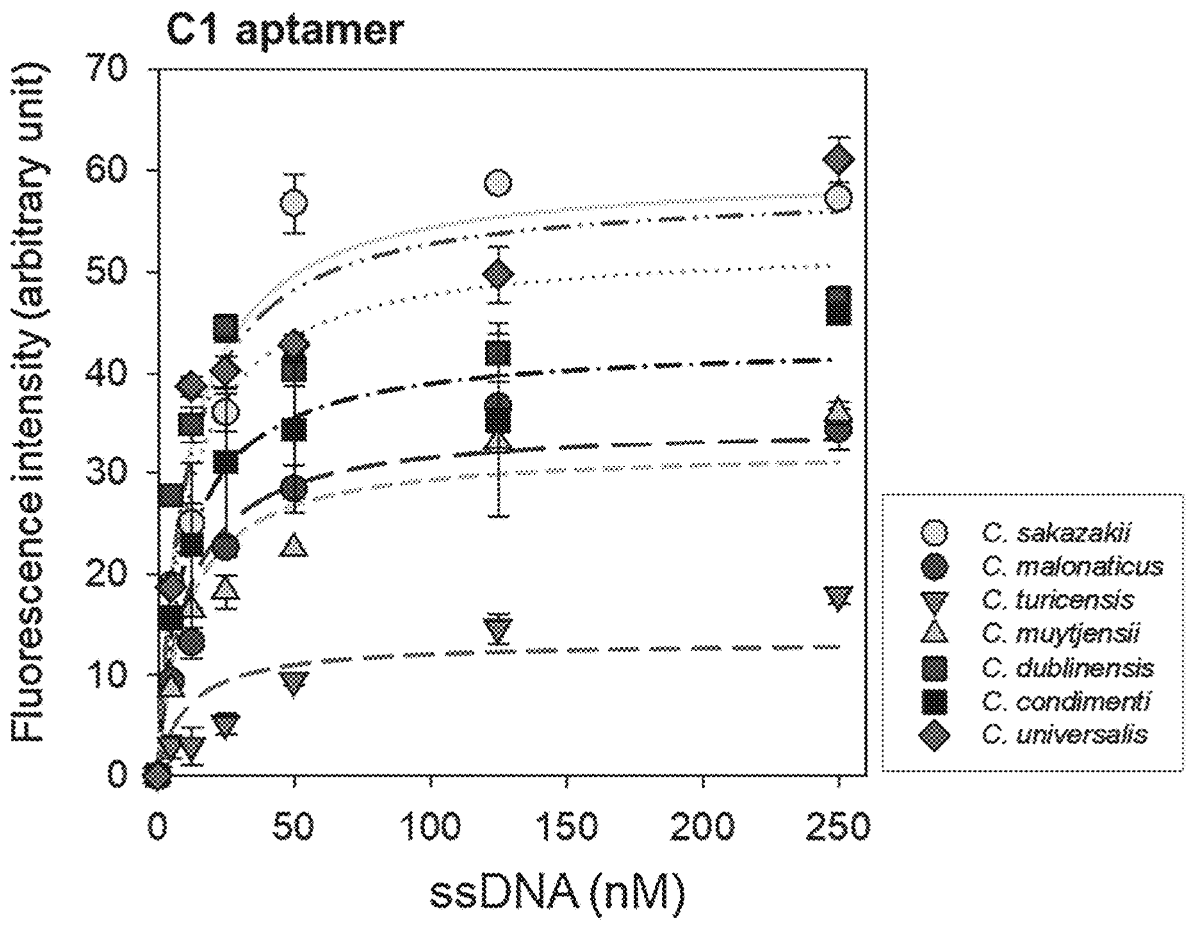
FIG. 4A is a diagram showing the results of analyzing the binding affinity of seven *Cronobacter* species-ssDNA aptamer (C1) complex.
Figure 4B:
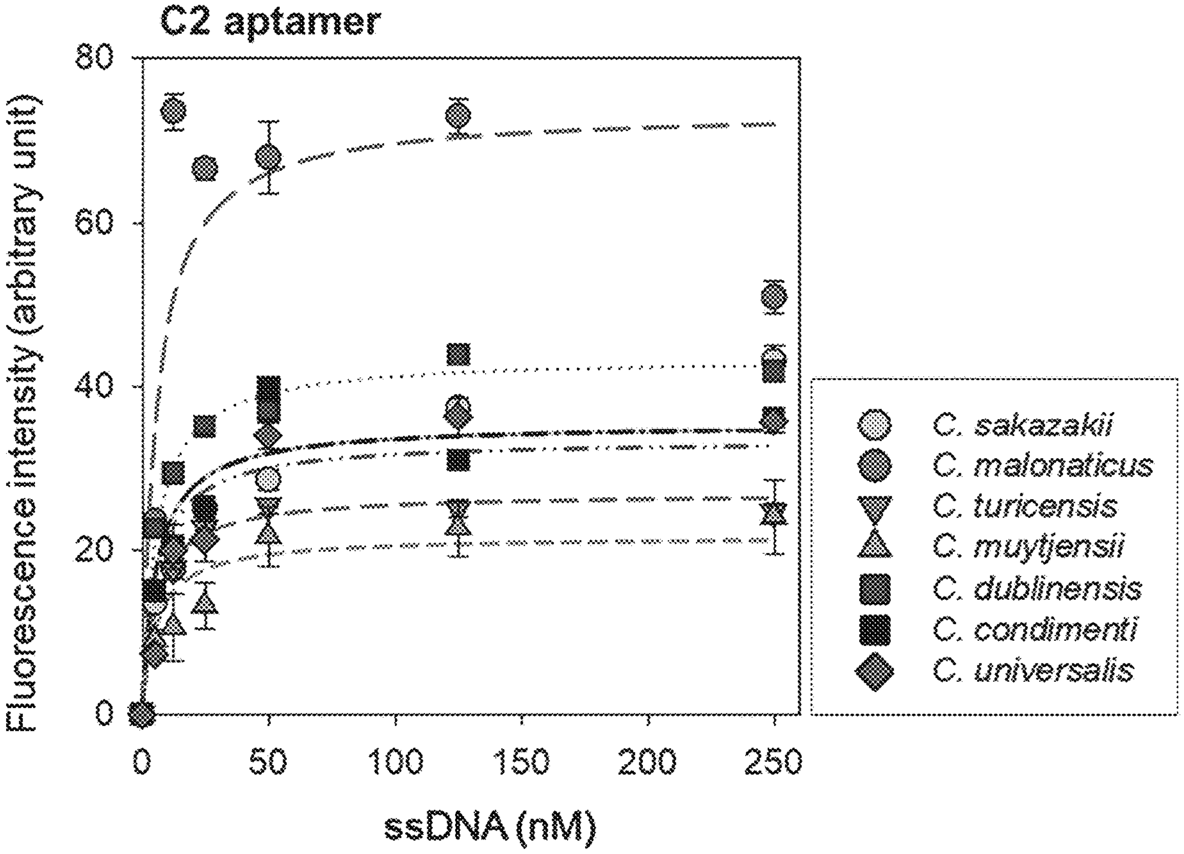
FIG. 4B is a diagram showing the results of analyzing the binding affinity of seven *Cronobacter* species-ssDNA aptamer (C2) complex.
Figure 4C:
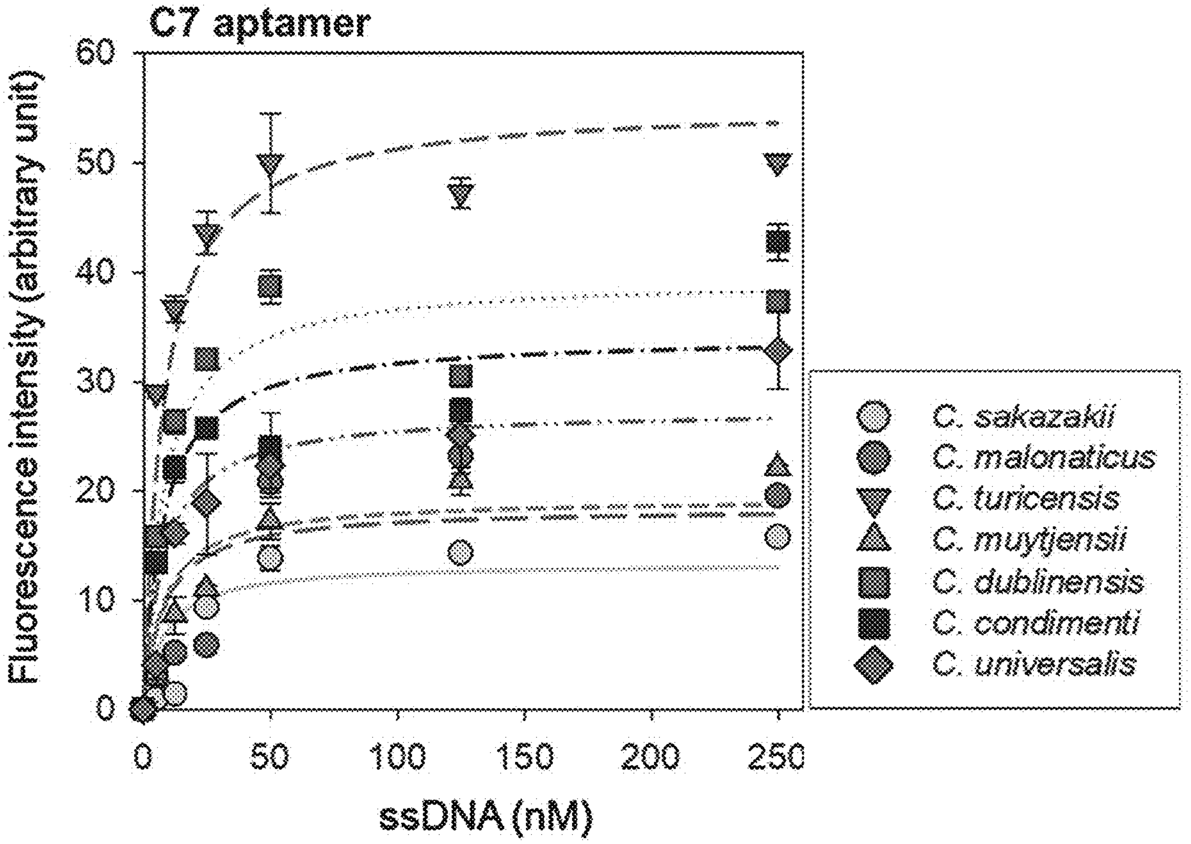
FIG. 4C is a diagram showing the results of analyzing the binding affinity of seven *Cronobacter* species-ssDNA aptamer (C7) complex.
Figure 4D:
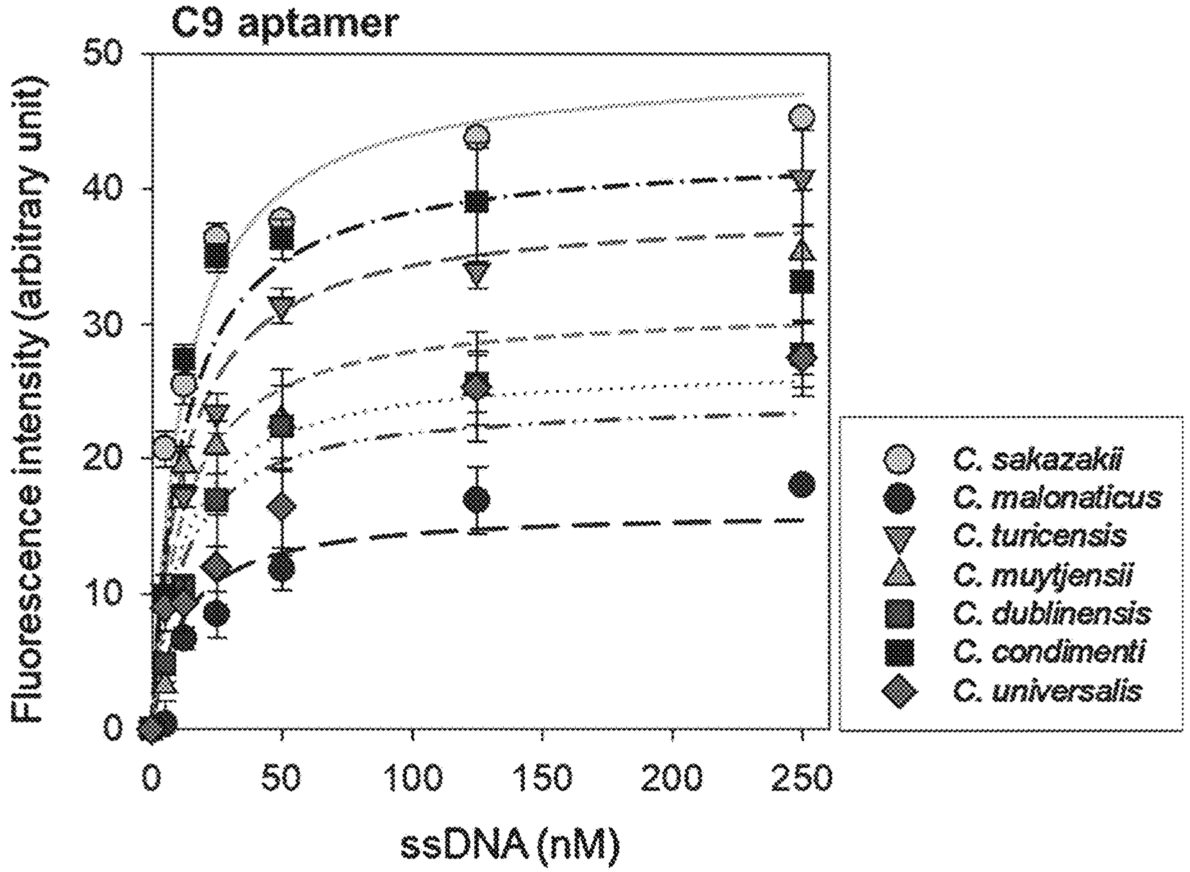
FIG. 4D is a diagram showing the results of analyzing the binding affinity of seven *Cronobacter* species-ssDNA aptamer (C9) complex.
Figure 5A:
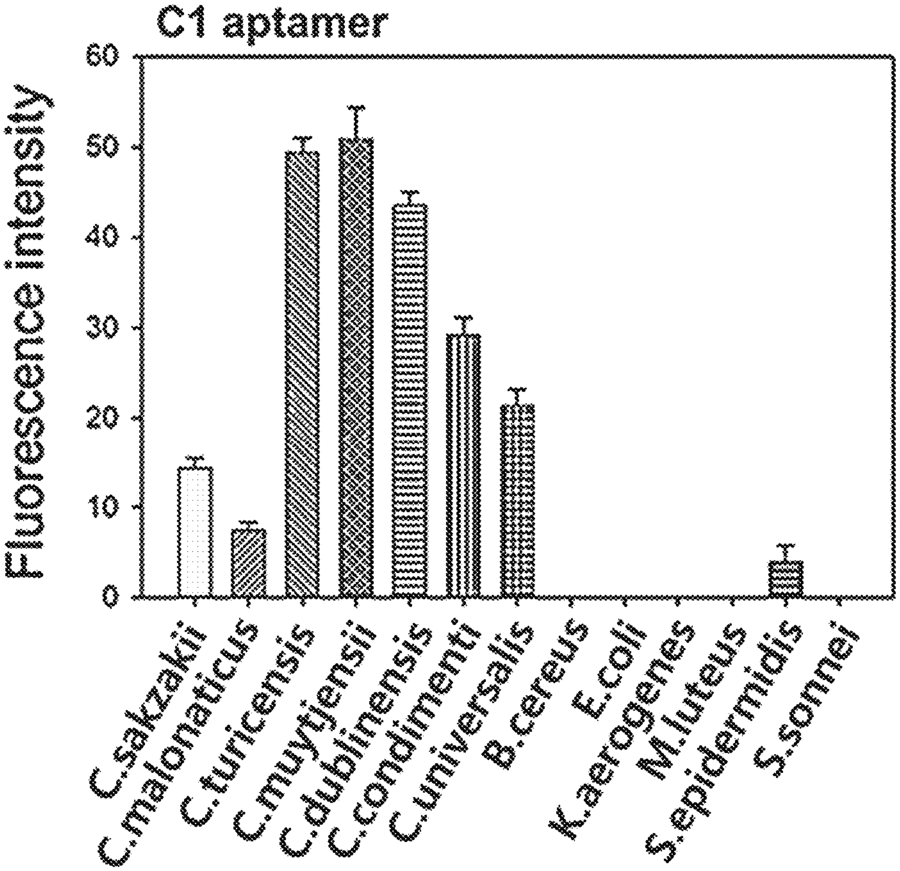
FIG. 5A is a diagram showing the results of analyzing the selectivity of ssDNA aptamer (C1) for seven *Cronobacter* species.
Figure 5B:
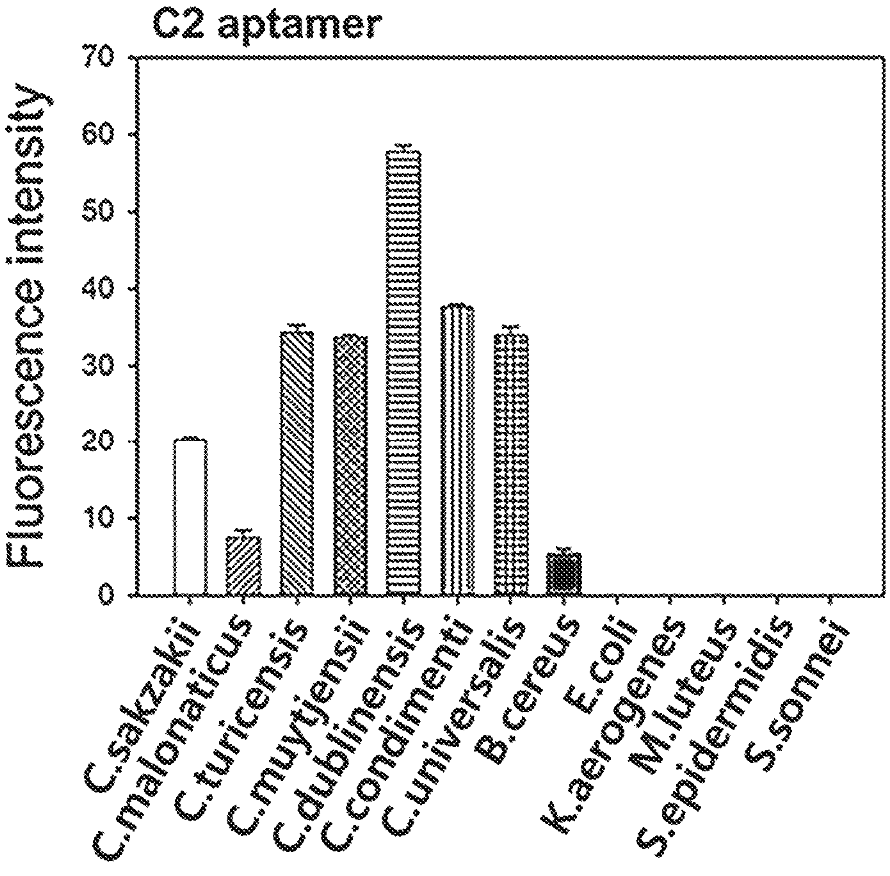
FIG. 5B is a diagram showing the results of analyzing the selectivity of ssDNA aptamer (C2) for seven *Cronobacter* species.
Figure 5C:
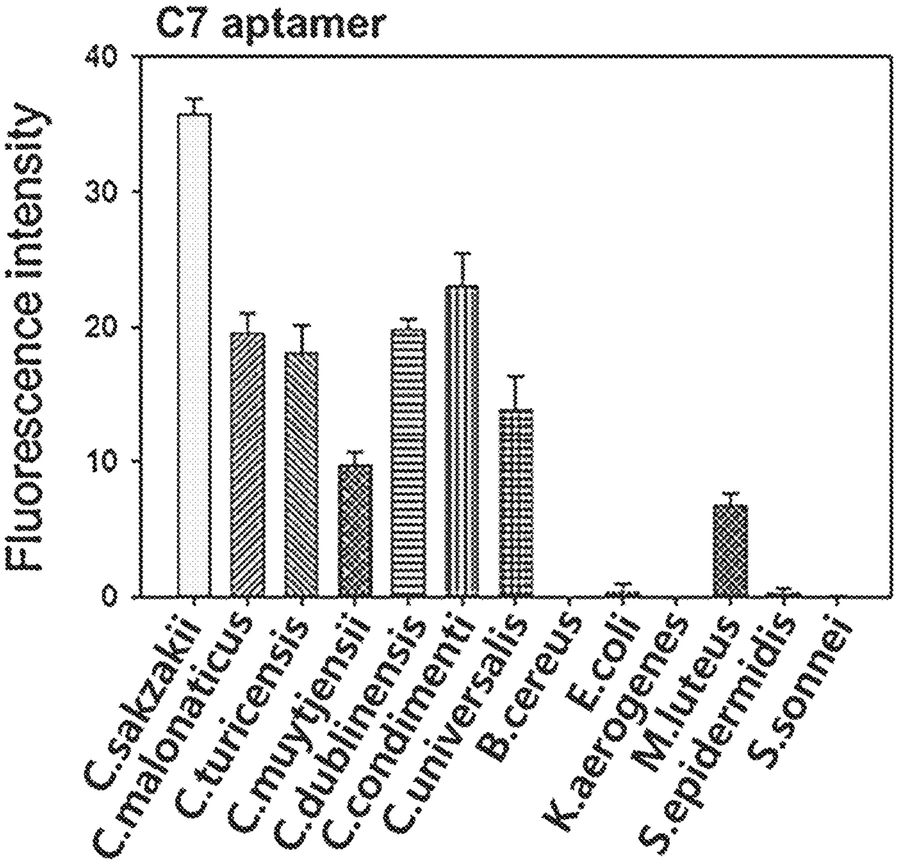
FIG. 5C is a diagram showing the results of analyzing the selectivity of ssDNA aptamer (C7) for seven *Cronobacter* species.
Figure 5D:
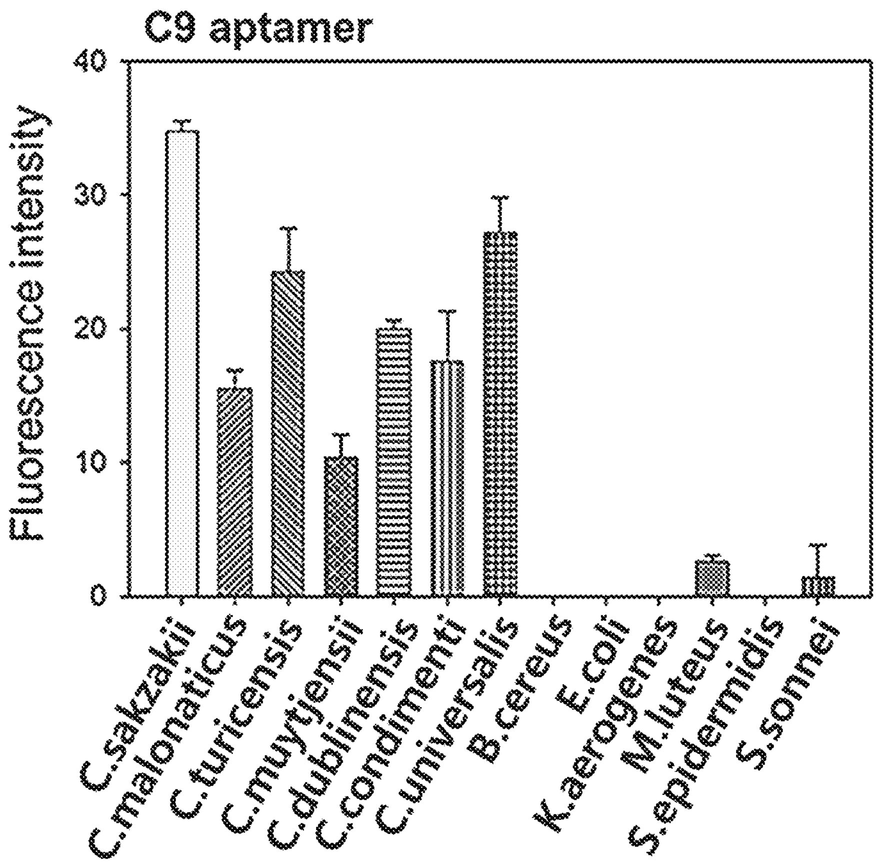
FIG. 5D is a diagram showing the results of analyzing the selectivity of ssDNA aptamer (C9) for seven *Cronobacter* species.

Hereinafter, preferred embodiments of the disclosure will be described in detail with reference to the accompanying drawings.

Embodiments of the present disclosure, which are disclosed in the present specification, are illustrated for the purpose of explanation only, and the embodiments of the present disclosure may be embodied in various embodiments and should not be construed as being limited to the embodiments described herein. The present disclosure allows for various changes and numerous embodiments, but the embodiments are not intended to limit the present disclosure to particular modes of practice, and are to be appreciated that all modifications, equivalents, and substitutes that do not depart from the spirit and technical scope of the present disclosure are encompassed. An expression used in the singular encompasses the expression of the plural, unless it has a clearly different meaning in the context. In the present specification, it is to be understood that the terms such as "comprising," and "having" are intended to indicate the existence of the features, numbers, steps, operations, elements, parts, or combinations thereof disclosed in the specification, and are not intended to preclude the possibility that one or more other features, numbers, steps, operations, elements, parts, or combinations thereof may exist or may be added.

In one aspect, the present disclosure may provide a single-stranded nucleic acid aptamer comprising at least one nucleotide sequence of nucleotide sequences of SEQ ID NOs: 1 to 4 shown in Table 1 below, and specifically binding to seven *Cronobacter* species consisting of *Cronobacter sakazakii, Cronobacter malonaticus, Cronobacter turicensis, Cronobacter muytjensii, Cronobacter dublinensis, Cronobacter condimenti* and *Cronobacter universalis.*

As used herein, the term "nucleic acid" is a polymer of nucleotides, and may be used in the same sense as oligonucleotide or polynucleotide. The nucleic acid may comprise deoxyribonucleotide (DNA), ribonucleotide (RNA), nucleotide analogue or peptide nucleic acid (PNA) molecule.

As used herein, the term "aptamer" refers to a nucleic acid molecule that has a stable tertiary structure and can bind to target substances such as heavy metals, organic compounds, proteins, bacteria, and cancer cells with specificity and affinity. For example, the aptamer may comprise a single-stranded DNA or RNA sequence.

As used herein, the term "specifically binding" means that the aptamer does not substantially bind to microorganisms other than *Cronobacter* or shows a large difference in affinity, enabling discrimination between *Cronobacter* and other microorganisms. The other microorganisms may comprise *Escherichia coli, Klebsiella aerogenes, Bacillus cereus, Micrococcus luteus, Staphylococcus epidermidis, Shigella sonnei* or the like.

TABLE 1

| ID | SEQ ID NO | Base sequence |
|---|---|---|
| C1 | 1 | CTAAGGCCCAGCAGTTTGAG GCG TCG ATG CTA CGT ATC AGA CCA AGT ATG TCG AAG GCG GTT CTA GTC CTA CGT TAA ATA TGC ATG GAT CGT TCA TGA GTG C GGACAGGGTTGGAAAAGTGA |
| C2 | 2 | CTAAGGCCCAGCAGTTTGAG GCG TCG ATG CTA CGT ATC AGA CCA AGT ATG TCG AAG GCG GTT TTA GTC CTA CGT TAA ATA TGC ATG GTT CGG GTT GGG TT GGACAGGGTTGGAAAAGTGA |
| C7 | 3 | CTAAGGCCCAGCAGTTTGAG GGC GAG GGA GTA AAG GAC GAA GAC GAT TGG TCA GTA TAG TTA GCA GGC GGA CGT ATC TAC TAG TTC AGG TAA TGC GCG CG GGACAGGGTTGGAAAAGTGA |
| C9 | 4 | CTAAGGCCCAGCAGTTTGAG GCG TCG ATG CTA CGT ATC AGA CCA AGT ATG TCG AAG GCG GTT TTA GTC CTA CGT CAA ATA TGC ATG GTT CGG GTT GGG TT GGACAGGGTTGGAAAAGTGA |

As an example, the aptamer may consist of the nucleotide sequence of SEQ ID NO: 1, SEQ ID NO: 2, SEQ ID NO: 3 or SEQ ID NO: 4.

In one embodiment, the aptamer may be obtained by substituting, inserting and/or deleting some nucleotides of any one nucleotide sequence selected from the group consisting of SEQ ID NO: 1 to SEQ ID NO: 4. For example, in the aptamer, some nucleotides not necessary for specific binding to the seven *Cronobacter* species among the nucleotide sequences may be substituted with other nucleotides. Specifically, the aptamer may have a sequence identity or homology of less than 100% to any one nucleotide sequence selected from the group consisting of SEQ ID NO: 1 to SEQ ID NO: 4. The sequence identity or homology may be defined as a percentage of the entire length of any one nucleotide sequence. For example, the aptamer may comprise a nucleotide sequence having 90% or more, 91% or more, 92% or more, 93% or more, 94% or more, 95% or more, 96% or more, 97% or more, 98% or more, 99% or more sequence identity or sequence homology with any one nucleotide sequence selected from the group consisting of SEQ ID NO: 1 to SEQ ID NO: 4.

In one embodiment, the single-stranded nucleic acid aptamer may be a single-stranded DNA (ssDNA) aptamer. In another embodiment, the single-stranded nucleic acid aptamer may be a single-stranded RNA (ssRNA) aptamer. In the case that the single-stranded nucleic acid aptamer is RNA, T is U in the nucleotide sequence.

In one embodiment, the aptamer may be prepared by chemically synthesizing any one nucleotide sequence selected from the group consisting of SEQ ID NO: 1 to SEQ ID NO: 4. Since the aptamer according to one embodiment is easily chemically synthesized, high purity and low cost mass production is possible.

In one embodiment, the aptamer may be obtained or screened by a method commonly used in the art. For example, the aptamer may be obtained through a systemic evolution of ligands by exponential enrichment (SELEX) method, a capillary based method, a nonequilibrium capillary electrophoresis of equilibrium mixtures (NECEEM) method, or the like.

The SELEX method is a screening method by maximizing specificity and affinity for a target substance by repeatedly adsorbing and desorbing a specific nucleotide sequence that binds to a target substance in vitro. Since repetitive experiments are required to obtain nucleotide sequences, the overall required time is long, making it difficult to respond quickly to the development of receptors required to rapidly detect acute contaminants or substances that cause acute infections. The capillary based method and the nonequilibrium capillary electrophoresis of equilibrium mixtures (NECEEM) method have been proposed to compensate for these disadvantages, but these methods acquire aptamers using small particles such as proteins and viruses as target substances. Therefore, there is a problem that it is not compatible with bacteria having a relatively large particle size. The centrifugation based-partitioning method is proposed to overcome this problem. From the random ssDNA library, ssDNA that is not attached to the target material and ssDNA with weak binding affinity are removed through an excessive desorption process using centrifugation in the stage of adsorption and desorption of bacterial surface, and a small amount of ssDNA with strong affinity and specificity can be screened. However, since the centrifugation-based partitioning method is a method for a single target substance, there is a limit to obtaining aptamers that can specifically bind to various bacteria.

In view of the above, according to one embodiment, the aptamer may be obtained or screened by a sequential partitioning method. In one embodiment, it is possible to rapidly obtain aptamers that specifically bind to all seven *Cronobacter* species in a short time by using the sequential partitioning method. Specifically, the method may comprise obtaining a base sequence having affinity with a first target bacterium, which is one of seven *Cronobacter* species, from a random ssDNA library; obtaining a nucleotide sequence having affinity with to a second target bacterium from the obtained nucleotide sequence; obtaining a nucleotide sequence having affinity with a third target bacterium from the obtained nucleotide sequence; obtaining a nucleotide sequence having affinity with to a fourth target bacterium from the obtained nucleotide sequence; obtaining a nucleotide sequence having affinity with a fifth target bacterium from the obtained nucleotide sequence; obtaining a nucleotide sequence having affinity with a sixth target bacterium from the obtained nucleotide sequence; and obtaining a nucleotide sequence having affinity with a seventh target bacterium from the obtained nucleotide sequence. In one embodiment, the step of obtaining a nucleotide sequence having affinity with the first target bacterium from the random ssDNA library may comprise combining the first target bacterium with the random ssDNA library; performing a partitioning step to remove the aptamer not attached to the first target bacterium; and obtaining a nucleotide sequence having affinity with the first target bacterium. In one embodiment, the step of obtaining a base sequence having affinity with the second, third, fourth, fifth, sixth or seventh target bacteria from the random ssDNA library, respectively, may be also performed in the same way as the step of obtaining the base sequence having affinity with the first target bacterium from the random ssDNA library. In one embodiment, the first to seventh target bacteria may be in the order of *Cronobacter sakazakii, Cronobacter malonaticus, Cronobacter turicensis, Cronobacter muytjensii, Cronobacter dublinensis, Cronobacter condimenti* and *Cronobacter universalis*. In one embodiment, in the sequential partitioning method, after obtaining a nucleotide sequence having affinity with the last target bacterium, selectivity for *Cronobacter* may be enhanced through a negative selection process. Bacteria used for the negative selection may comprise *Escherichia coli, Klebsiella aerogenes, Bacillus cereus, Micrococcus luteus, Staphylococcus epidermidis* and/or *Shigella sonnei*, the nucleotide sequences that bind to these bacteria are removed, and only base sequences that do not bind to these bacteria can be separated and proceeded. The step of amplifying the nucleotide sequence obtained in the negative selection using PCR and finally acquiring the aptamer through cloning and sequencing may be further comprised.

FIG. 1 is a schematic diagram of a sequential partitioning method for producing and selecting single-stranded nucleic acid aptamers according to an embodiment of the disclosure, and FIG. 2 shows a schematic diagram of a SELEX method as another method. As shown in FIG. 2, in the SELEX method, receptors having affinity to each *Cronobacter* target substance are selected and then must be subjected to an amplification process through PCR. Thus, there is disadvantage that it takes a relatively long time, and thus it is not possible to quickly obtain the receptors for detecting new pathogenic substances or substances already damaged by the pathogenic substances. On the other hand, the sequential partitioning method as shown in FIG. 1 may comprise attaching a random DNA receptor to the first *Cronobacter* target substance (*C. sakazakii*); removing receptors that are not attached to the *Cronobacter* target substance through a centrifugation-based partitioning process; selecting a receptor having affinity to the first *Cronobacter* target substance and sequentially attaching the receptor to the next *Cronobacter* target substance (*C. malonaticus*); after performing the same process with the third, fourth, fifth and sixth *Cronobacter* target substances, selecting a receptor having affinity to the last *Cronobacter* target substance (*C. universalis*) and performing amplification using a polymerase chain reaction (PCR). Thus, it is possible to extract multi-sensing DNA receptors for detecting the seven *Cronobacter* species faster than the conventional SELEX method. In one embodiment, the aptamer may have a detectable label attached thereto. The detectable label may be used without limitation as long as it can be detected by a detection method known in the art. Specifically, the detectable label may be an optical label, an electrochemical label, a radioactive isotope, or a combination thereof. More specifically, the label may be attached to a specific base of the aptamer, to a specific structure such as a hairpin-loop structure, or to the 3' or 5' end of the aptamer. In one embodiment, the optical label may be, for example, a fluorescent substance. For example, the fluorescent substance may be selected from the group consisting of fluorescein, 6-carboxyfluorescein (6-FAM™), rhodamine, sulforhodamine 101 acid chloride (Texas Red®), tetramethylrhodamine, carboxyrhodamine, carboxyrhodamine 6G, carboxyrhodol, carboxyrhodamine 110, acetylated pyrene trisulfonic acid (Cascade Blue®), pyridyloxazole derivatives (Cascade Yellow®), coumarin, carbocyanine (Cy2™), indocarbocyanine (Cy3™), ndocarbocyanine derivatives (Cy3.5™), indodicarbocyanine (Cy5™), indodicarbocyanine derivatives (Cy5.5™), cyanine-chromium complex (Cy-chromium™), phycoerythrin, peridinine chlorophyll-a protein (PerCP™), peridinine chlorophyll-indodicarbocyanine derivatives conjugate (PerCP-Cy5.5R), 6-carboxy-4',5'-dichloro-2',7'-dimethoxyfluorescein (JOE™), benzofluor fluorophore (NED™), 5-(and-6)-carboxy-X-rhodamine (ROX™), hexachlorofluorescein (HEX™), naphthalimide dye (Lucifer Yellow®), 6,8-difluoro-7-hydroxycoumarin derivative (Marina Blue™), fluorinated fluoresceins (Oregon Green 488® Oregon Green 500®, Oregon Green 514®), sulfonated xanthene or coumarin dyes (Alexa Fluor®), 7-amino-4-methylcomarin-3-acetic acid, boron-dipyrromethene derivatives (BODIPY FLO, BODIPYR FL-Br 2, BODIPY® 530/550), conjugates thereof, and combinations thereof.

More specifically, the fluorescent substance may be fluorescein, indocarbocyanine (Cy3™) or indodicarbocyanine (Cy5™). In one embodiment, the optical label comprises a fluorescent donor chromophore and a fluorescent acceptor chromophore separated by an appropriate distance, and may be a fluorescence resonance energy transfer (FRET) pair in which the fluorescence of the donor is suppressed by the acceptor. In one embodiment, the fluorescent donor chromophore may comprise one or more selected from the group consisting of 6-carboxyfluorescein (FAM™), carboxytetramethylrhodamine (TAMRA™), chlorinated fluorescein derivative (VIC™), 4,5-dichloro-dimethoxy-fluorescein (JOE™), indocarbocyanine (Cy3™), indodicarbocyanine (Cy5™), and sulforhodamine 101 acid chloride (Texas Red®). In one embodiment, the fluorescent acceptor chromophore may be selected such that its excitation spectrum overlaps the donor's emission spectrum. In one embodiment, the acceptor may be a non-fluorescent acceptor that quenches a wide range of donors. Examples of other donor-acceptor FRET pairs known in the art may also be comprised in the present specification. In one embodiment, the electrochemical label may comprise an electrochemical label known in the art, and for example, the electrochemical label may be methylene blue.

In another aspect, the disclosure may provide a composition for detecting *Cronobacter*, which comprises the single-stranded nucleic acid aptamer according to one embodiment described above and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis*.

In still another aspect, the disclosure may provide a kit for detecting *Cronobacter*, which comprises the single-stranded nucleic acid aptamer according to one embodiment described above and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis*.

In still another aspect, the disclosure may provide a biosensor for detecting *Cronobacter*, which comprises the single-stranded nucleic acid aptamer according to one embodiment described above and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis*. In one embodiment, the biosensor for detecting *Cronobacter* may comprise the above described kit.

The kit or biosensor according to one embodiment may be for simultaneously detecting at least one, at least two, at least three, at least four, at least five, at least six, or at least seven *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis*. Also, according to one embodiment, the kit or biosensor may be for simultaneously detecting and removing the *Cronobacter.*

In the kit or biosensor according to one embodiment, the single-stranded nucleic acid aptamer may be comprised in the composition for detecting *Cronobacter.*

The composition, kit, or biosensor according to one embodiment may further comprise a reaction buffer, and the reaction buffer is not limited as long as it is commonly used in the art.

In the kit or biosensor according to one embodiment, the single-stranded nucleic acid aptamer may be immobilized on a substrate. In this case, the aptamer may be directly immobilized on the substrate or by a linker. In the specification, the substrate refers to a support capable of immobilizing or storing the aptamer comprised in the detection kit or sensor. The substrate may be, for example, a bead, a membrane, a microtiter plate, or a chip, and any substrate commonly used in the art may be comprised without being limited to the type. In one embodiment, the bead may be a magnetic bead.

The kit or biosensor according to one embodiment may further comprise an instruction describing a method of detecting, or detecting and removing *Cronobacter* in a sample using the above-described aptamer.

In still another aspect, the disclosure may provide a method for detecting one or more *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis* from a sample by using the single-stranded nucleic acid aptamer according to one embodiment described above.

In still another aspect, the disclosure may provide a method for removing one or more *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis* from a sample by using the single-stranded nucleic acid aptamer according to one embodiment described above.

In one embodiment, a method for detecting the *Cronobacter* from a sample may comprise contacting the single-stranded nucleic acid aptamer with a sample; and identifying whether a *Cronobacter*-aptamer complex is formed by contact of the single-stranded nucleic acid aptamer with *Cronobacter* in the sample.

In one embodiment, a method for removing the *Cronobacter* from a sample may comprise contacting the single-stranded nucleic acid aptamer with a sample to form a complex of two or more *Cronobacter* species and the single-stranded nucleic acid aptamer; and removing the complex.

In one embodiment, the detection method or removal method may be to multiplex detection or multiple detection and removal of one or more, two or more, three or more, four or more, five or more, six or more, or seven or more *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

In one embodiment, the detection method or removal method may comprise the use of the composition, kit, or sensor according to one embodiment described above. That is, in one embodiment, the aptamer may be provided in the form of the above-described composition or kit. The aptamer may be immobilized on a substrate. The substrate may be a bead, a membrane, a microtiter plate, or a chip.

In one embodiment, the sample refers to a substance in which *Cronobacter* may exist, and the type of substance is not limited. For example, the sample may comprise food, drinking water, river, seawater, wastewater, soil, waste, air, waste, samples separated from the human body, samples collected from animals or plants, or the like. In one embodiment, the sample may be infant formula powder.

In one embodiment, the step of contacting the single-stranded nucleic acid aptamer with a sample in the detection method or the step of contacting the single-stranded nucleic acid aptamer with a sample to form a complex of two or more *Cronobacter* species and the single-stranded nucleic acid aptamer in the removal method may comprise dropping a solution containing the sample onto a container or substrate containing the single-stranded nucleic acid aptamer to contact the single-stranded nucleic acid aptamer with the sample, mixing the solution containing the single-stranded nucleic acid aptamer and the solution containing the sample, or the like. However, as long as the single-stranded nucleic acid aptamer can be brought into contact with the sample, the method is not limited thereto.

In one embodiment, the contact may be performed under a condition in which the single-stranded nucleic acid aptamer and *Cronobacter* in the sample are contacted so that the two bind to form a *Cronobacter*-aptamer complex. For example, the step may comprise adjusting reaction pH, reaction temperature, reaction time, or the like for binding of the single-stranded nucleic acid aptamer to the *Cronobacter* in the sample. The pH may be, for example, 5 or more, 6 or more, 7 or more, or 8 or more, and may be 8.5 or less, 8 or less, 7 or less, or 6 or less, but is not limited thereto. The reaction temperature may be, for example, 5° C. or more, 10° C. or more, 15° C. or more, 20° C. or more, 25° C. or more, 30° C. or more, 35° C. or more, 40° C. or more, 45° C. or more, or 49° C. or more, and may be 50° C. or less, 45° C. or less, 40° C. or less, 35° C. or less, 30° C. or less, 25° C. or less, 20° C. or less, 15° C. or less, 10° C. or less, or 6° C. or less, but is not limited thereto. The reaction time may be, for example, 10 minutes or more, 15 minutes or more, 20 minutes or more, 25 minutes or more, 30 minutes or more, 35 minutes or more, 40 minutes or more, 45 minutes or more, or 50 minutes or more, and may be 60 minutes or less, 55 minutes or less, 50 minutes or less, 45 minutes or less, 40 minutes or less, 35 minutes or less, 30 minutes or less, 25 minutes or less, 20 minutes or less, or 15 minutes or less, but is not limited thereto.

In one embodiment, the removal method may further comprise, after contacting the single-stranded nucleic acid aptamer and the sample to form the complex of *Cronobacter* and the single-stranded nucleic acid aptamer, identifying whether the *Cronobacter*-aptamer complex is formed by contact between the single-stranded nucleic acid aptamer and *Cronobacter* in the sample before the step of removing the complex or after the step of removing the complex.

In one embodiment, in the detection method or removal method, the step of identifying whether the *Cronobacter*-aptamer complex is formed by contact between the single-stranded nucleic acid aptamer and *Cronobacter* in the sample may comprise measuring a signal from the *Cronobacter*-aptamer complex formed by contacting the single-stranded nucleic acid aptamer with the sample; and identifying a presence or concentration of the *Cronobacter* in the sample from the measured signal.

In one embodiment, any method of measuring a signal commonly used in the art may be used as the step of measuring the signal without limitation. For example, the method may include measuring one or more of an optical signal, an electrochemical signal, a radioactive isotope, and an enzyme signal. Specifically, the optical signal may include fluorescence intensity.

In one embodiment, the step of identifying a presence or concentration of *Cronobacter* in the sample from the measured signal may be performed by comparing with a control group. The control group may be *Cronobacter* not treated with the aptamer.

In one embodiment, the step of removing the complex may comprise removing the single-stranded nucleic acid aptamer from the sample by detaching the single-stranded nucleic acid aptamer. In this case, the detachment may include separating the *Cronobacter* and the single-stranded nucleic acid aptamer from the complex of the *Cronobacter* and the single-stranded nucleic acid aptamer. In one embodiment, the detachment may be performed by washing, filtration, adsorption, centrifugation, magnetism, or a combination thereof, but is not limited thereto.

As a conventional method for detecting *Cronobacter*, a real-time PCR method using primers for detecting *Cronobacter sakazakii* has been generally used, but this method has disadvantages in that the pretreatment (e.g., DNA extraction) of detection sample is required to detect a genetic marker, and a professional operator capable of professionally operating PCR is required for PCR analysis. However, according to one embodiment of the disclosure, it has the advantage of being able to target seven *Cronobacter* species, that is, multiple target substances, and detecting target substances using actual samples without sample pretreatment such as DNA extraction. In addition, the conventional method of inoculating animals with *Cronobacter* to obtain primary antibody, IgG, and detecting *Cronobacter* using an immune-based assay requires animal experiments to obtain primary and secondary antibodies for detecting the *Cronobacter* strain. Thus, this method has the disadvantage of taking a long time and being vulnerable to environmental factors due to the nature of the antibody, which is a receptor for the target substance. On the other hand, according to one embodiment of the disclosure, since the receptor for a target substance is a single-stranded nucleic acid aptamer, it is structurally and environmentally stable, and has the advantage of being able to obtain or prepare a single-stranded nucleic acid aptamer in a short time.

Hereinafter, the disclosure will be described in detail with reference to the following examples. However, the following examples are provided only for illustrative purpose to help in the understanding of the disclosure, and the scope and range of the disclosure are not limited thereto.

[Example 1] Preparation of Aptamers That Specifically Bind to Seven *Cronobacter* Species In one embodiment of the disclosure, aptamers that specifically bind to seven *Cronobacter* species were screened in a sequential manner, as shown in FIG. 1, by selecting receptors without the PCR enrichment step by performing the attachment and detachment process between a random DNA library and a target substance, and re-attaching and re-detaching of the receptor selected for the target substance in the previous step to the next target substance. The finally isolated receptor was amplified using one-time PCR, and cloning and sequencing were performed to obtain receptors (aptamer candidates) having affinity with the seven *Cronobacter* species. The specific method is as follows.

1. ssDNA Library Synthesis

A random ssDNA library composed of the following single-stranded DNA oligonucleotides was synthesized. The synthesized random ssDNA library has a total length of 120 nucleotides, and has a nucleotide sequence region in which primer pairs are fixed at both ends for cloning and a nucleotide sequence region randomly arranged in the center.

```
                                    (SEQ ID NO: 5)
5'-CTAAGGCCCAGCAGTTTGAG-N(80)-

GGACAGGGTTGGAAAAGTGA-3'
```

Here, N(80) generally means consisting of 80 random A, G, T, and C bases, but the number of bases is not necessarily limited to 80. Any number of bases in 80 may be added or omitted by the PCR and cloning process, and thus the overall length of the ssDNA library may be changed.

2. Mixing With Culture Medium of Seven *Cronobacter* Species and Separating ssDNA Seven *Cronobacter* species (*Cronobacter sakazakii* (KCTC 2949), *Cronobacter malonaticus* (LMG 23826), *Cronobacter turicensis* (LMG 23827), *Cronobacter muytjensii* (ATCC 51329), *Cronobacter dublinensis* (LMG 23823), *Cronobacter condimenti* (LMG 26250), and *Cronobacter universalis* (LMG 26249)), which were target substances for mixing with the random ssDNA library, were each inoculated into nutrient broth, and then cultured at 37° C. until each concentration reached $5\times10^8$ CFU/mL. Next, in order to remove the culture medium from the solution in which each of the seven *Cronobacter* species was cultured, the culture medium was washed three times using 1× phosphate-buffered saline (PBS) buffer, and then suspended in a binding buffer (1×PBS, 0.05% Tween 20, 5 mM $MgCl_2$, 0.45 g glucose). Thereafter, the random ssDNA library was dissolved in the binding buffer and heated at 95° C. for 5 minutes, immediately lowered the temperature to 4° C. using ice, and then, was added with the first substance (*Cronobacter sakazakii*) suspension ($5\times10^7$ CFU) suspended in binding buffer and mixed for 1 hour at room temperature. Thereafter, the ssDNAs not bound to *Cronobacter sakazakii* were removed using a centrifuge at 13000 rpm for 3 minutes, suspended in a elution buffer (1×PBS, 5 mM $MgCl_2$, 0.45 g glucose), and the *Cronobacter sakazakii*-ssDNA mixture was heat-treated. Thus, the ssDNA attached to the surface of *Cronobacter sakazakii*, the first target substance, was isolated from *Cronobacter sakazakii*. Then, the second target substance (*Cronobacter malonaticus*) suspension ($5\times10^7$ CFU) and the ssDNA attached to the surface of *Cronobacter sakazakii* and isolated were mixed and combined for 1 hour at room temperature. After that, the ssDNAs not bound to *Cronobacter malonaticus* were removed using a centrifuge, suspended in a elution buffer, and then heat-treated to isolate the ssDNAs attached to the surface of *Cronobacter malonaticus*, the second target material, from *Cronobacter malonaticus*. Afterwards, the selection process with the third target substance (*Cronobacter turicensis*) was sequentially performed, and the order of section of the seven *Cronobacter* species was *Cronobacter sakazakii, Cronobacter malonaticus, Cronobacter turicensis, Cronobacter muytjensii, Cronobacter dublinensis, Cronobacter condimenti* and *Cronobacter universalis.*

3. Negative Selection Process

The ssDNAs isolated from the last target substance (*Cronobacter universalis*) may bind to the seven *Cronobacter* species, but there is a possibility that the cell surface substances are present in other bacteria other than the seven *Cronobacter* species, so for the ssDNAs isolated from the last target substance, the negative selection using other bacteria was performed once. Bacteria used for the negative selection were *Escherichia coli, Bacillus cereus, Shigella sonnei, Klebsiella aerogenes, Staphylococcus epidermidis*, and *Micrococcus luteus*. The ssDNAs binding to these bacteria were removed, and only ssDNAs that did not bind to these bacteria were isolated.

4. PCR Amplification and Purification

The ssDNAs collected through the negative selection process were amplified through PCR. The sequences of the primers used in this case were shown in Table 2 below.

TABLE 2

| | SEQ ID NO | Sequence (5' → 3') |
|---|---|---|
| Forward primer | 6 | CTAAGGCCCAGCAGTTTGAG |
| Reverse primer | 7 | TCACTTTTCCAACCCTGTCC |

Specifically, PCR was performed twice in total to amplify the ssDNAs collected through the negative selection process. A PCR mixture was composed of 20 μL of the solution containing the ssDNA collected through the negative selection process, 2.5 μL (10 μM) of each of the primers in Table 2, and 25 μL of the PCR master mix. PCR was performed in a total amount of 50 μL of the PCT mixture. The temperature conditions were 95° C. for 30 seconds, 55° C. for 30 seconds, and 72° C. for 30 seconds, and the PCR was repeated 15 times. In order to determine that the PCR was successfully performed, PCR products were analyzed by electrophoresis using a 3% agarose gel. A second PCR mixture was composed of 20 μL of dsDNA amplified through the above PCR, 2.5 μL (20 μM) of each of the primers in Table 2, and 25 μL of PCR master mix, and PCR was performed in a total amount of 50 μL of the second PCR mixture. The temperature conditions were the same as the first PCR method, but PCR was repeated 10 times. PCR products were finally purified using a PCR purification kit (MinElute PCR Purification Kit, Qiagen). The final PCR products were cloned using a cloning kit (TOPO TA cloning kit), and plasmids cloned from each colony were extracted using a plasmid extraction kit and subjected to nucleotide sequencing. Among the obtained sequences, four ssDNA aptamers predicted to have the highest binding affinity with the seven *Cronobacter* species were selected through homology analysis by the Mfold program (http://www.unafold.org/mfold/applications/dna-folding-form.php) and multiple sequence alignment program (https://www.genome.jp/tools-bin/clustalw), and were shown in Table 3. FIGS. 3*a* to 3*d* are diagrams showing the 2D structure analysis of each ssDNA aptamer (C1, C2, C7, C9) of Table 3 using the above programs.

TABLE 3

| ID | SEQ ID NO | Base sequence |
|---|---|---|
| C1 | 1 | CTAAGGCCCAGCAGTTTGAG GCG TCG ATG CTA CGT ATC AGA CCA AGT ATG TCG AAG GCG GTT CTA GTC CTA CGT TAA ATA TGC ATG GAT CGT TCA TGA GTG C GGACAGGGTTGGA AAAGTGA |
| C2 | 2 | CTAAGGCCCAGCAGTTTGAG GCG TCG ATG CTA CGT ATC AGA CCA AGT ATG TCG AAG GCG GTT TTA GTC CTA CGT TAA ATA TGC ATG GTT CGG GTT GGG TT GGACAGGGTTGGAAAA GTGA |
| C7 | 3 | CTAAGGCCCAGCAGTTTGAG GGC GAG GGA GTA AAG GAC GAA GAC GAT TGG TCA GTA TAG TTA GCA GGC GGA CGT ATC TAC TAG TTC AGG TAA TGC GCG CG GGACAGGGTTGGAAAA GTGA |
| C9 | 4 | CTAAGGCCCAGCAGTTTGAG GCG TCG ATG CTA CGT ATC AGA CCA AGT ATG TCG AAG GCG GTT TTA GTC CTA CGT CAA ATA TGC ATG GTT CGG GTT GGG TT GGACAGGGTTGGAAAA GTGA |

[Example 2] Analysis of Binding Affinity of Aptamer to Seven *Cronobacter* Species The affinity of the ssDNA (C1, C2, C7, and C9) sequences selected in Example 1 to seven *Cronobacter* species, which were target substances, was analyzed according to the following method.

The seven *Cronobacter* species (*Cronobacter sakazakii* (KCTC 2949), *Cronobacter malonaticus* (LMG 23826), *Cronobacter turicensis* (LMG 23827), *Cronobacter muytjensii* (ATCC 51329), *Cronobacter dublinensis* (LMG 23823), *Cronobacter condimenti* (LMG 26250), and *Cronobacter universalis* (LMG 26249)) were each inoculated into a culture medium, and then cultured at 37° C. until each concentration reached $5\times10^8$ CFU/mL. Then, after washing three times using 1×PBS buffer to remove the culture medium from each inoculated culture medium, it was suspended in 1×PBS buffer. 100 μL of the seven *Cronobacter* species ($5\times10^7$ CFU) were respectively mixed with 100 μL of fluorescently labeled ssDNA (0, 10, 25, 50, 100, 250, 500 nM) at various concentrations, and reacted at room temperature for 30 minutes. After the reaction, the culture medium was washed three times with 1×PBS buffer to remove the ssDNAs not bound to the surfaces of the seven *Cronobacter* species and then the fluorescence intensity of each of the seven *Cronobacter* species-ssDNA complex was measured using fluorimeter (DeNovix QFX fluorometer, Wilmington DE, USA). FIGS. 4*a* to 4*d* are diagrams illustrating the analysis of the fluorescence intensity measurement results of the seven *Cronobacter* species 7-ssDNA (C1, C2, C7 or C9) complexes. The fluorescence intensity at each ssDNA concentration condition was plotted using a nonlinear regression method and a single-region saturation ligand binding method via a SigmaPlot program, and the $K_d$ value was calculated using Equation 1 below, and summarized and listed in Table 4.

$$F=B_{max}*C/(K_d+C) \quad \text{[Equation 1]}$$

In the above Equation, F is the fluorescence intensity, $B_{max}$ is the maximum binding intensity, $K_d$ is the dissociation constant, and C is the ssDNA concentration.

TABLE 4

| | *Cronobacter sakazakii* | *Cronobacter malonaticus* | *Cronobacter turicensis* | *Cronobacter muytjensii* | *Cronobacter dublinensis* | *Cronobacter condimenti* | *Cronobacter universalis* |
|---|---|---|---|---|---|---|---|
| C1 | 15.7 | 21.8 | 86.6 | 23 | 3.5 | 10.1 | 8.8 |
| C2 | 18.1 | 3.6 | 4 | 14.7 | 5.5 | 8.8 | 16.5 |
| C7 | 33.5 | 39.6 | 3.7 | 26.3 | 6 | 10 | 22.9 |
| C8 | 8.3 | 40.8 | 17.7 | 16.5 | 24.2 | 8.6 | 30.8 |

From the above results, the binding affinity ($K_d$, dissociation constant) for the seven *Cronobacter* species was measured from a minimum of 3.6 nM to a maximum of 86.6 nM, indicating that the ssDNA aptamer according to the disclosure exhibited a high level of binding affinity for the seven *Cronobacter* species.

[Example 3] Selectivity Analysis of Aptamer for Seven *Cronobacter* Species

In order to determine the selectivity of the ssDNA (C1, C2, C7, C9) aptamer selected in Example 1 for seven *Cronobacter* species, the selectivity compared and analyzed with 6 other species of bacteria other than *Cronobacter.*

As the other six bacteria, *Escherichia coli* (KCTC 2571), *Bacillus cereus* (KCTC 3711), *Shigella sonnei* (KCTC 2518), *Klebsiella aerogenes* (KCTC 2190), *Staphylococcus epidermidis* (KCTC 13171) and *Micrococcus luteus* (KCTC 9857) (KCTC: Korea Collection for Type Cultures) were used.

In the experiment, 100 μL of each bacteria ($5\times10^7$ CFU) and 100 μL of 50 nM ssDNA (C1, C2, C7 or C9) were reacted at room temperature for 30 minutes, washed with 1×PBS buffer, and the fluorescence intensity of each bacteria-ssDNA (C1, C2, C7 or C9) complex was measured and compared with. The fluorescence intensity was measured and analyzed in the same manner as in Example 2 above. The analyzed results were integrated with the results of Example 2 and were shown in FIGS. 5A to 5D, respectively.

As shown in FIGS. 5A to 5D, the fluorescence intensity of the complex of the selected ssDNA aptamer and seven *Cronobacter* species, which were the target of the disclosure, and the fluorescence intensity of the complex of the selected ssDNA aptamer and six other bacteria were compared. As a result, the ssDNA aptamer (C1, C2, C7, C9) according to one embodiment of the disclosure exhibited much higher fluorescence intensity for the seven *Cronobacter* species than for *Bacillus cereus, Escherichia coli, Klebsiella aerogenes, Micrococcus luteus, Staphylococcus epidermidis, Shigella sonnei*, so that it can be determined that the ssDNA aptamer (C1, C2, C7, C9) has significant selectivity for the seven *Cronobacter* species.

[Example 4] Detection of Seven *Cronobacter* Species in a Sample

In order to verify the availability of the ssDNA aptamer selected in Example 1 for the seven *Cronobacter* species, the experiment was conducted by referring to the method for detecting *Cronobacter* spp. provided by the Korea Food and Drug Administration (Food Codex: Article 8 General Test Method—4. Microbial Test Method—4.21 *Enterobacter sakazakii* (*Cronobacter* spp.)), which is incorporated herein by reference.

Figure 6:
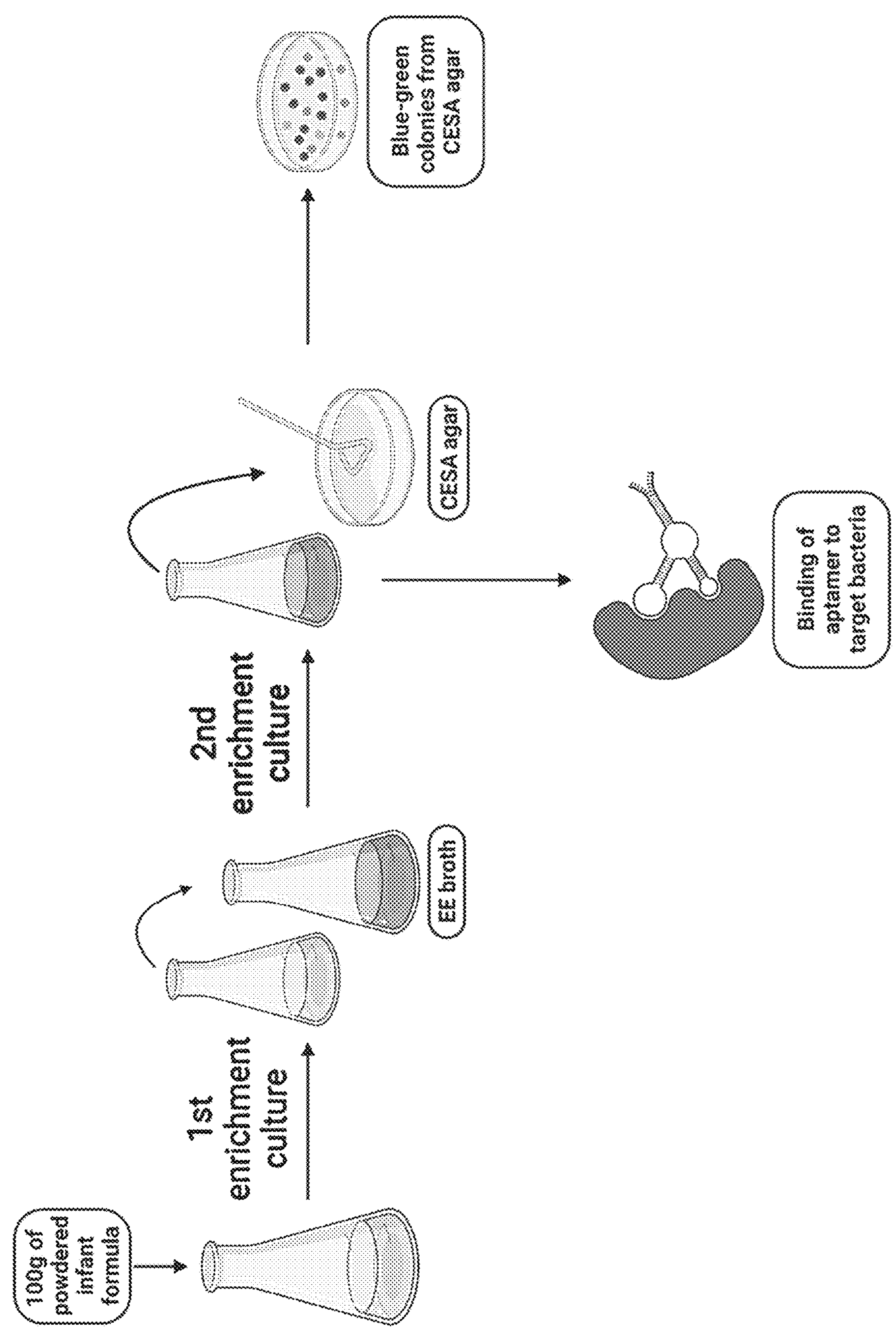
FIG. 6 is a schematic diagram showing the detection method of *Cronobacter* spp. provided by the Korea Food and Drug Administration and the method using the screened ssDNA aptamer used in one embodiment of the disclosure.

First, as shown in FIG. 6, a primary culture was performed by inoculating 100 μL of a mixture of the seven *Cronobacter* species identical to the mixture used in Example 2 and 100 μL of the mixed solution ($10^0$, $10^1$, $10^2$, $10^3$, $10^4$ CFU) for the bacteria used in the negative selection in Example 3 into infant formula powder (Absolute Myungjak, Maeil Dairies) dissolved in water, respectively, and incubating at 37° C. for 24 hours. Then, a secondary culture was performed by inoculating 100 μL of the primary culture medium in a *Cronobacter* selective medium (EE broth, Oxoid, Hampshire, UK) and incubating at 37° C. for 24 hours. Thereafter, 100 μL of a portion of the cultured secondary culture medium was transferred to CESA agar medium (Oxoid), a selective medium for *Cronobacter*, and incubated at 37° C. for 24 hours. Then, blue-green colonies were identified, which were shown in FIG. 7A.

Separately, in one embodiment of the disclosure, a primary culture was performed by inoculating 100 μL of a mixture of the seven *Cronobacter* species identical to the mixture used in Example 2 into infant formula powder (Absolute Myungjak, Maeil Dairies) dissolved in water, and incubating at 37° C. for 24 hours. Then, a secondary culture was performed by inoculating 100 μL of the primary culture medium in a *Cronobacter* selective medium (EE broth, Oxoid, Hampshire, UK) and incubating at 37° C. for 24 hours. Thereafter, unlike the method for detecting *Cronobacter* spp. provided by the Korea Food and Drug Administration detection method, colonies were not finally identified, and 100 μL of the cultured secondary culture medium (EE broth) was immediately mixed with 500 nM ssDNA aptamer (C1, C2, C7, C9) selected in Example 1 and subjected to an attachment process for 1 hour. Thereafter, the aptamers not attached to the cultured secondary culture medium (EE broth) were detached using a centrifuge, and the fluorescence intensity of the bacteria-ssDNA aptamer complex was analyzed and shown in FIG. 7B. In this case, the fluorescence intensity was analyzed using the same method as described in Example 2 above.

In the disclosure, by using the selected ssDNA aptamers (C1, C2, C7, C9), it is possible to reduce the time consumed by additional culture to select *Cronobacter*, and to avoid secondary contamination damage caused by multiple cultures.

Figure 7A:
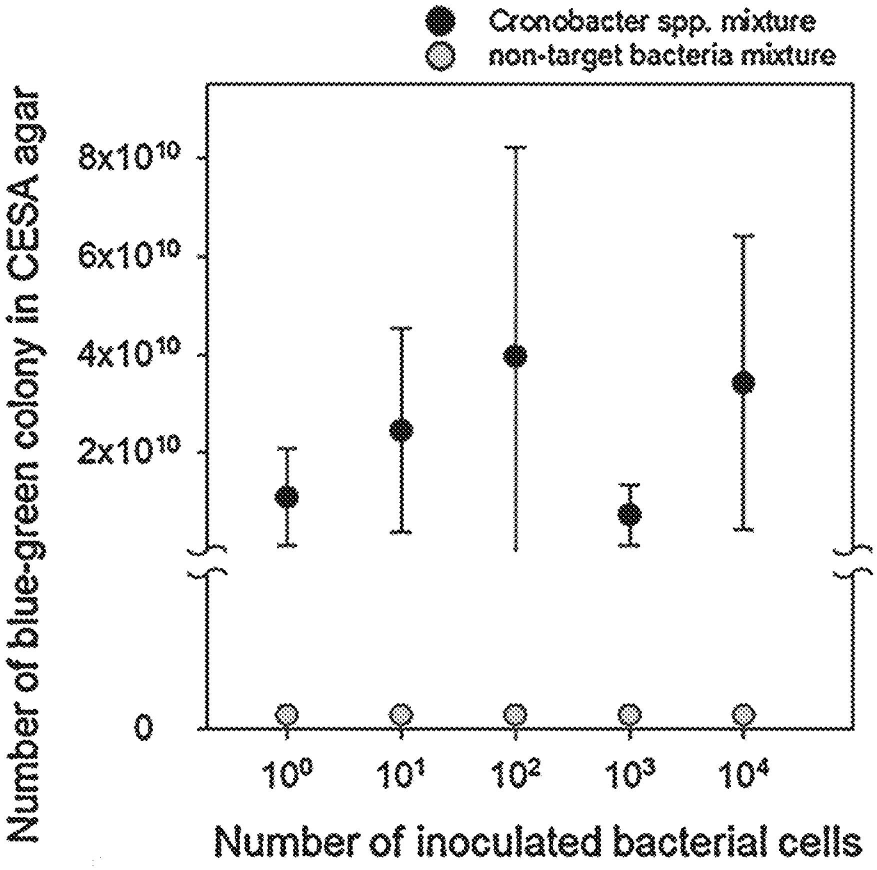
FIG. 7A is a diagram showing the number of blue-green colonies cultured on CESA agar medium of each inoculated sample measured using the method provided by the Korea Food and Drug Administration in Example 4.

FIG. 7A shows the number of blue-green colonies cultured on CESA agar of each inoculated sample using the method provided by the Korea Food and Drug Administration. Due to the characteristics of the CESA agar medium, which is a *Cronobacter* selective medium, the *Cronobacter* strain formed blue-green colonies. That is, as a result of identifying the number of cultured colonies, it can be seen that blue-green colonies are formed only in the sample inoculated with *Cronobacter.*

Figure 7B:
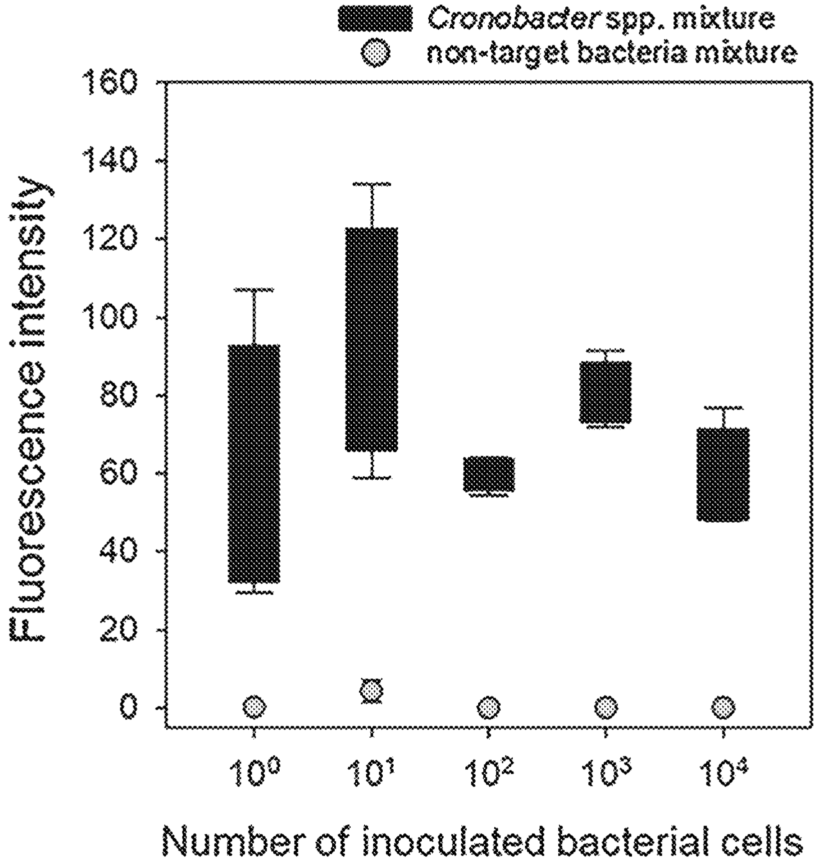
FIG. 7B is a diagram showing the range of fluorescence intensity measured from a mixture of ssDNA aptamers (C1, C2, C7, C9) screened according to the present disclosure in Example 4 and secondary cultured selective medium (EE broth).

FIG. 7B shows the range of fluorescence intensity measured in a mixture of ssDNA aptamers (C1, C2, C7, C9) selected according to the disclosure and secondary cultured selective medium (EE broth). As a result of measuring the fluorescence intensity, the fluorescence intensity was measured to be high in the sample inoculated with the seven *Cronobacter* species. This is because the ssDNA aptamers (C1, C2, C7, and C9) selected according to the disclosure bind specifically to the seven *Cronobacter* species in other media to form a complex, which means that the seven *Cronobacter* species can be easily and quickly detected without additional culture.

[Example 5] Detection and Selectivity Analysis of Aptamers for Seven *Cronobacter* Species in a Sample In order to determine whether the ssDNA aptamers (C1, C2, C7, C9) selected according to one embodiment of the disclosure can specifically detect the seven *Cronobacter* species in various bacterial communities, the following experiment was performed.

Specifically, except for the inoculation of 100 μL of a mixture of the seven *Cronobacter* species identical to the mixture used in Example 2 and 100 μL of the mixed solution ($10^0$, $10^1$, $10^2$, $10^3$, $10^4$ CFU) for the bacteria used in the negative selection in Example 3 into infant formula powder (Absolute Myungjak, Maeil Dairies) dissolved in water, the primary and secondary cultures were performed in the same manner as in the method according to one embodiment of the disclosure used in Example 4. Thereafter, the cultures were mixed with ssDNA aptamers (C1, C2, C7, C9) and subjected to an attachment process for 1 hour. Thereafter, the aptamer not attached to the cultured secondary culture medium (EE broth) was detached using a centrifuge, and the fluorescence intensity of the bacteria-ssDNA aptamer complex was analyzed and shown in FIG. 8.

Figure 9:
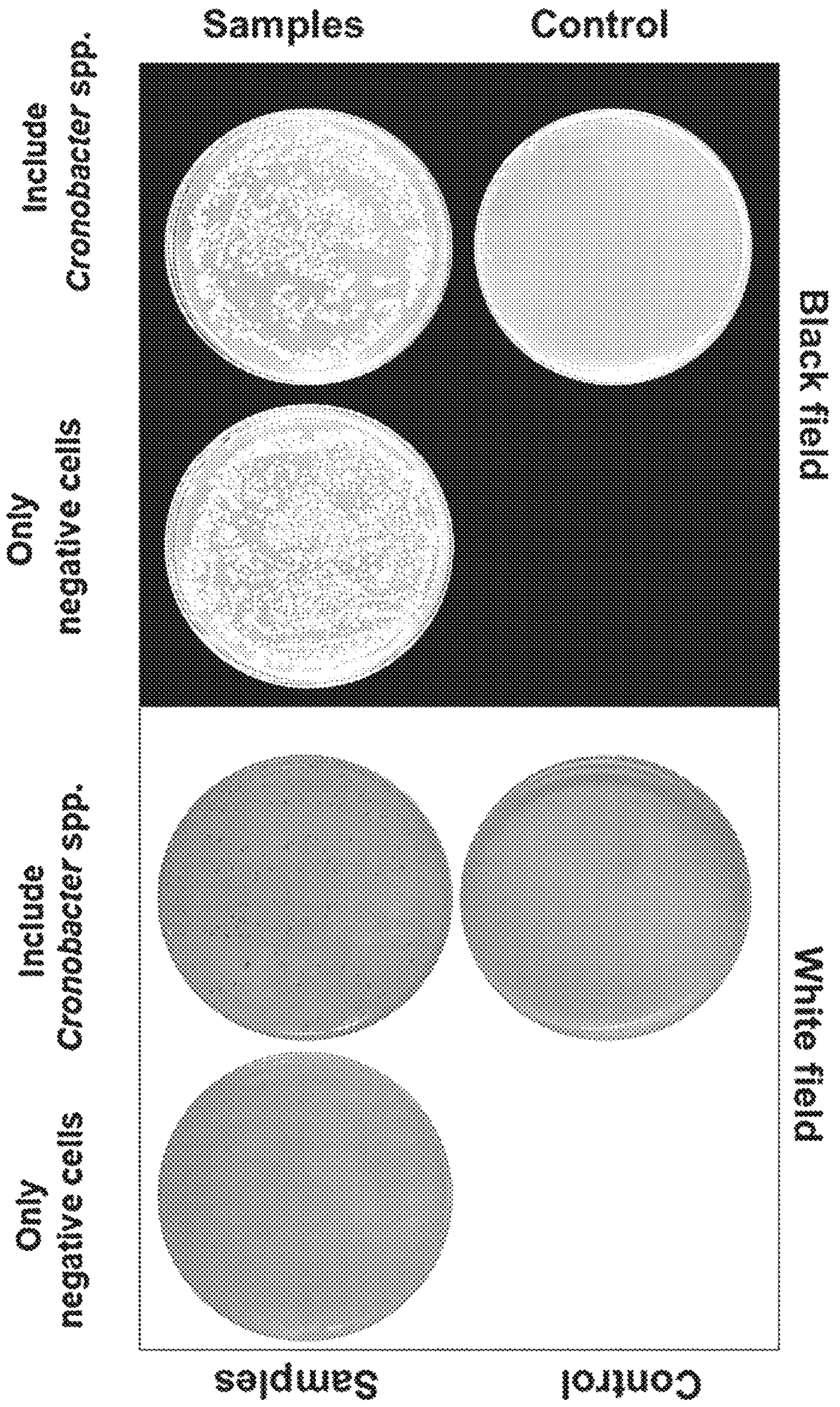
FIG. 9 shows photographed images of blue-green colonies representing *Cronobacter* and white colonies representing general bacteria to identify the presence of seven *Cronobacter* species in various clusters of the culture medium cultured in Example 5.

FIG. 9 shows photographed images of blue-green colonies identified after transferring 100 μL of a portion of the cultured secondary culture medium to CESA agar medium (Oxoid), a selective medium for *Cronobacter*, and incubating at 37° C. for 24 hours, in order to determine whether the seven *Cronobacter* species are present in various clusters of the culture medium. It was difficult to simultaneously photograph the blue-green colonies representing *Cronobacter* and the white colonies representing general bacteria, so images were taken when the background was dark and not dark. As a result, it was confirmed that blue-green colonies were detected in the clusters comprising the seven *Cronobacter* species.

Figure 8:
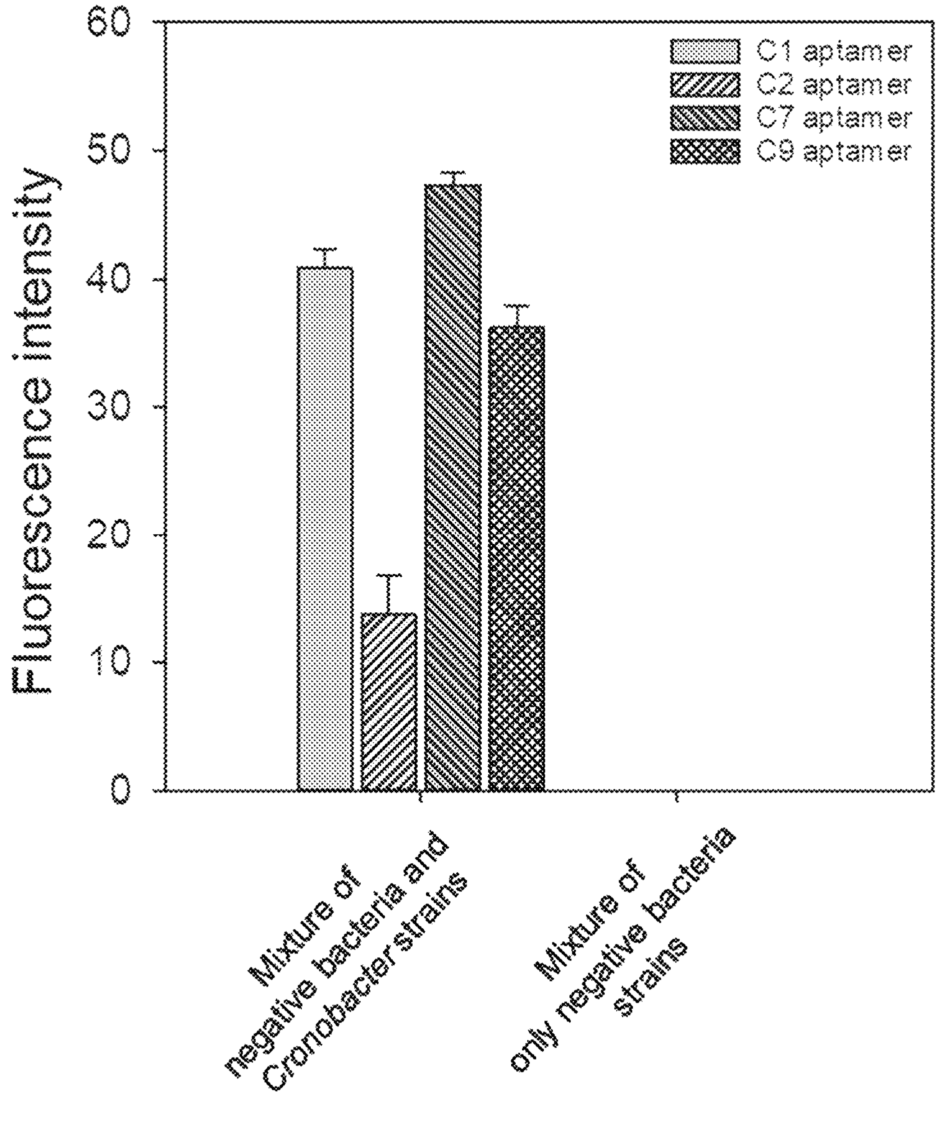
FIG. 8 is a diagram showing the analysis of whether ssDNA aptamers (C1, C2, C7, C9) screened according to one embodiment of the present disclosure in Example 5 can specifically detect seven *Cronobacter* species within various bacterial communities by fluorescence intensity measurement.

From FIGS. 8 and 9, it can be seen that the fluorescence intensity was measured in the sample comprising the seven *Cronobacter* species, which indicates that the ssDNA aptamer (C1, C2, C7, C9) according to the disclosure can specifically detect the seven *Cronobacter* species in multiplex.

The disclosure may provide the following embodiments as one embodiment.

First embodiment may provide a single-stranded nucleic acid aptamer comprising at least one nucleotide sequence of nucleotide sequences of SEQ ID NOs: 1 to 4, and specifically binding to seven *Cronobacter* species consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Second embodiment provide the single-stranded nucleic acid aptamer of First embodiment wherein in a case that the single-stranded nucleic acid aptamer is RNA, T is U in the nucleotide sequence.

Third embodiment may provide the single-stranded nucleic acid aptamer of First or Second embodiment wherein the single-stranded nucleic acid aptamer has a detectable label attached thereto.

Fourth embodiment may provide a composition for multi-detection of *Cronobacter*, which comprises the single-stranded nucleic acid aptamer of any one of First to Third embodiments and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Fifth embodiment may provide a kit for detecting *Cronobacter*, which comprises the single-stranded nucleic acid aptamer of any one of First to Third embodiments and detects one or more selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Six embodiment may provide the kit of Fifth embodiment wherein the single-stranded nucleic acid aptamer is immobilized on a substrate.

Seventh embodiment may provide the kit of Fifth or Sixth embodiment wherein the substrate is a bead, a membrane, a microtiter plate, or a chip.

Eighth embodiment may provide the kit of any one of Fifth to Seventh embodiments wherein the kit is to detect the seven *Cronobacter* species simultaneously.

Ninth embodiment may provide the kit of any one of Fifth to Eighth embodiments wherein the kit is to detect and remove the one or more *Cronobacter* species simultaneously.

Tenth embodiment may provide a biosensor comprising the composition or kit of any one of Fourth to Ninth embodiments.

Eleventh embodiment may provide a method for detecting *Cronobacter*, comprising contacting the single-stranded nucleic acid aptamer of any one of First to Third embodiments with a sample; and identifying whether a *Cronobacter*-aptamer complex is formed by contact of the single-stranded nucleic acid aptamer with *Cronobacter* in the sample.

Twelfth embodiment may provide the method of Eleventh embodiment wherein the step of identifying whether the complex is formed comprises measuring a signal from the *Cronobacter*-aptamer complex formed by contacting the single-stranded nucleic acid aptamer with the sample; and identifying a presence or concentration of the *Cronobacter* in the sample from the measured signal.

Thirteenth embodiment may provide the method of Eleventh or Twelfth embodiment wherein the method is to detect one or more *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

Fourteenth embodiment may provide the method of any one of Eleventh to Thirteenth embodiments wherein the step of measuring the signal is to measure fluorescence intensity.

Fifteenth embodiment may provide a method for removing *Cronobacter* from a sample comprising contacting the single-stranded nucleic acid aptamer of any one of First to Third embodiments with a sample to form a complex of *Cronobacter* and the single-stranded nucleic acid aptamer; and removing the complex.

Sixteenth embodiment may provide the method of Fifteenth embodiment wherein the step of removing the complex is to detach and remove the single-stranded nucleic acid aptamer from the sample.

Seventeenth embodiment may provide the method of Fifteenth or Sixteenth embodiment wherein the method is for removing one or more *Cronobacter* selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

What is claimed is:

1. A single-stranded nucleic acid aptamer comprising at least one nucleotide sequence selected from the group consisting of SEQ ID NOs: 1 to 4, and specifically binding to *Cronobacter* species selected from the group consisting of *Cronobacter sakazakii, Cronobacter malonaticus, Cronobacter turicensis, Cronobacter muytjensii, Cronobacter dublinensis, Cronobacter condimenti* and *Cronobacter universalis.*

```
                         SEQUENCE LISTING

Sequence total quantity: 7
SEQ ID NO: 1            moltype = DNA  length = 122
FEATURE                 Location/Qualifiers
source                  1..122
                        mol_type = other DNA
                        organism = unidentified
SEQUENCE: 1
ctaaggccca gcagtttgag gcgtcgatgc tacgtatcag accaagtatg tcgaaggcgg  60
ttctagtcct acgttaaata tgcatggatc gttcatgagt gcggacaggg ttggaaaagt  120
ga                                                                 122

SEQ ID NO: 2            moltype = DNA  length = 120
FEATURE                 Location/Qualifiers
source                  1..120
                        mol_type = other DNA
                        organism = unidentified
SEQUENCE: 2
ctaaggccca gcagtttgag gcgtcgatgc tacgtatcag accaagtatg tcgaaggcgg  60
ttttagtcct acgttaaata tgcatggttc gggttgggtt ggacagggtt ggaaaagtga  120

SEQ ID NO: 3            moltype = DNA  length = 120
FEATURE                 Location/Qualifiers
source                  1..120
                        mol_type = other DNA
                        organism = unidentified
SEQUENCE: 3
ctaaggccca gcagtttgag ggcgagggag taaaggacga agacgattgg tcagtatagt  60
tagcaggcgg acgtatctac tagttcaggt aatgcgcgcg ggacagggtt ggaaaagtga  120

SEQ ID NO: 4            moltype = DNA  length = 120
FEATURE                 Location/Qualifiers
source                  1..120
                        mol_type = other DNA
                        organism = unidentified
SEQUENCE: 4
ctaaggccca gcagtttgag gcgtcgatgc tacgtatcag accaagtatg tcgaaggcgg  60
ttttagtcct acgtcaaata tgcatggttc gggttgggtt ggacagggtt ggaaaagtga  120

SEQ ID NO: 5            moltype = DNA  length = 120
FEATURE                 Location/Qualifiers
source                  1..120
                        mol_type = other DNA
                        organism = synthetic construct
SEQUENCE: 5
ctaaggccca gcagtttgag nnnnnnnnnn nnnnnnnnnn nnnnnnnnnn nnnnnnnnnn  60
nnnnnnnnnn nnnnnnnnnn nnnnnnnnnn nnnnnnnnnn ggacagggtt ggaaaagtga  120

SEQ ID NO: 6            moltype = DNA  length = 20
FEATURE                 Location/Qualifiers
source                  1..20
                        mol_type = other DNA
                        organism = synthetic construct
SEQUENCE: 6
ctaaggccca gcagtttgag                                              20

SEQ ID NO: 7            moltype = DNA  length = 20
FEATURE                 Location/Qualifiers
source                  1..20
                        mol_type = other DNA
                        organism = synthetic construct
SEQUENCE: 7
tcacttttcc aaccctgtcc                                              20
```

2. The single-stranded nucleic acid aptamer of claim 1, wherein when the single-stranded nucleic acid aptamer is RNA, T is substituted with U in the nucleotide sequence.

3. The single-stranded nucleic acid aptamer of claim 1, wherein the single-stranded nucleic acid aptamer has a detectable label attached thereto.

4. A composition for multi-detection of *Cronobacter*, which comprises the single-stranded nucleic acid aptamer of claim 1, wherein the single-stranded nucleic acid aptamer has a detectable label attached thereto.

5. The composition of claim 4, wherein when the single-stranded nucleic acid aptamer is RNA, T is substituted with U in the nucleotide sequence.

6. A kit for detecting *Cronobacter*, which comprises the single-stranded nucleic acid aptamer of claim 1, wherein the single-stranded nucleic acid aptamer is immobilized on a substrate.

7. The kit of claim 6, wherein the substrate is a bead, a membrane, a microtiter plate, or a chip.

8. The kit of claim 6, wherein when the single-stranded nucleic acid aptamer is RNA, T is substituted with U in the nucleotide sequence.

9. The kit of claim 6, wherein the single-stranded nucleic acid aptamer has a detectable label attached thereto.

10. A biosensor comprising the kit of claim 6.

* * * * *